United States Patent
Kim et al.

(10) Patent No.: US 12,073,016 B2
(45) Date of Patent: Aug. 27, 2024

(54) ELECTRONIC DEVICE AND METHOD OF OPERATING THE SAME

(71) Applicant: SAMSUNG ELECTRONICS CO., LTD., Suwon-si (KR)

(72) Inventors: Doyoun Kim, Suwon-si (KR); Harry Edward Milton, Suwon-si (KR); Bonkon Koo, Suwon-si (KR); Sangho Yoon, Suwon-si (KR); Youngmo Jeong, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 165 days.

(21) Appl. No.: 17/678,613

(22) Filed: Feb. 23, 2022

(65) Prior Publication Data
US 2022/0269342 A1 Aug. 25, 2022

Related U.S. Application Data

(63) Continuation of application No. PCT/KR2022/002508, filed on Feb. 21, 2022.

(30) Foreign Application Priority Data

Feb. 23, 2021 (KR) .................. 10-2021-0024366

(51) Int. Cl.
*G06F 3/01* (2006.01)
*G02B 27/00* (2006.01)
(Continued)

(52) U.S. Cl.
CPC ......... *G06F 3/013* (2013.01); *G02B 27/0093* (2013.01); *G02B 27/0172* (2013.01);
(Continued)

(58) Field of Classification Search
None
See application file for complete search history.

(56) References Cited

U.S. PATENT DOCUMENTS 6,769,770 B2 8/2004 Fink et al.
7,220,000 B2 5/2007 Alster et al.
(Continued)

FOREIGN PATENT DOCUMENTS

JP 4626980 B2 2/2011
JP 5688491 B2 3/2015
(Continued)

OTHER PUBLICATIONS

Search Report (PCT/ISA/220, PCT/ISA/210) issued May 26, 2022 by the International Searching Authority in International Patent Application No. PCT/KR2022/002508.
(Continued)

*Primary Examiner* — Jwalant Amin
(74) *Attorney, Agent, or Firm* — Sughrue Mion, PLLC

(57) ABSTRACT

Provided is an electronic device for detecting lost portions of a field of vision and distorted portions of a field of vision and storing these in a vision map. The lost portions and distorted portions are identified in cooperation with the user by means of virtual image superposition on a real scene, audible requests to the user, gesture inputs provided by the user and gaze tracking. The electronic device may detect an object and provide visual information to a user when the object is in a lost portion or distorted portion of the field of vision.

13 Claims, 28 Drawing Sheets

(51) Int. Cl.
*G02B 27/01* (2006.01)
*A61B 3/024* (2006.01)
*A61B 3/032* (2006.01)

(52) U.S. Cl.
CPC .............. *G06F 3/011* (2013.01); *G06F 3/017* (2013.01); *A61B 3/024* (2013.01); *A61B 3/032* (2013.01); *G02B 2027/0125* (2013.01); *G02B 2027/0138* (2013.01)

(56) References Cited

U.S. PATENT DOCUMENTS

| | | | |
|---|---|---|---|
| 7,699,466 | B2 | 4/2010 | Hayakawa et al. |
| 9,844,317 | B2 | 12/2017 | Green |
| 10,451,877 | B2 | 10/2019 | Samec et al. |
| 10,890,767 | B1 | 1/2021 | Fernandez |
| 11,160,688 | B2 | 11/2021 | Cho et al. |
| 2002/0013573 | A1 | 1/2002 | Telfair et al. |
| 2017/0000332 | A1* | 1/2017 | Samec ................... A61B 5/361 |

FOREIGN PATENT DOCUMENTS

| | | |
|---|---|---|
| KR | 10-2016-0024986 A | 3/2016 |
| KR | 10-2019-0105487 A | 9/2019 |
| KR | 1020190126895 A | 11/2019 |
| KR | 10-2020-0136297 A | 12/2020 |

OTHER PUBLICATIONS

Written Opinion (PCT/ISA/237) issued May 26, 2022 by the International Searching Authority in International Patent Application No. PCT/KR2022/002508.

* cited by examiner

FIG. 1B
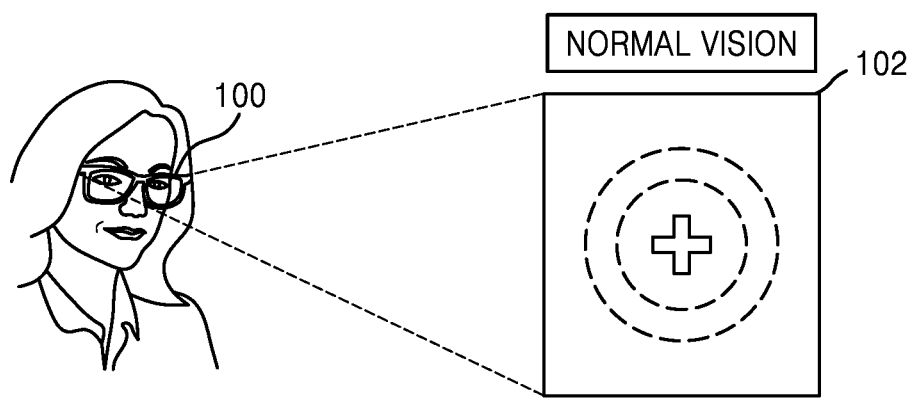
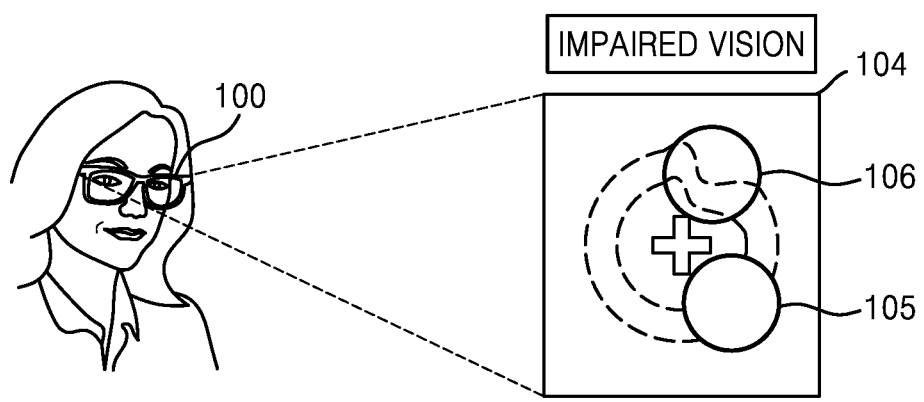

ELECTRONIC DEVICE AND METHOD OF OPERATING THE SAME

CROSS-REFERENCE TO RELATED APPLICATION

This application is a by-pass continuation of international application PCT/KR2022/002508 filed on Feb. 21, 2022 and claims benefit of priority to Korean Patent Application No. 10-2021-0024366 filed on Feb. 23, 2021.

TECHNICAL FIELD

The disclosure relates to an electronic device for diagnosing visual impairment of a user and providing assistance to the user with visual impairment while providing an augmented reality (AR) service.

BACKGROUND ART

Augmented reality (AR) is a technology for overlaying a virtual image on a physical environment space of the real world or on a real world object, so as to be displayed as a single image. An AR device which is worn on the face or head of a user allows the user to see a real scene and a virtual image together through a see-through display module provided in front of the eyes of the user.

Research on a method of easily and accurately diagnosing visual impairment of the user by using the AR device when the user of the AR device has visual impairment is required.

In addition, research on a method of minimizing inconvenience caused by visual impairment when providing an AR service to the user with visual impairment is also required.

DESCRIPTION OF EMBODIMENTS

Technical Problem

Provided are an electronic device for diagnosing visual impairment of a user, and a method of operating the same.

Provided are an electronic device for providing assistance to a user with visual impairment, and a method of operating the same.

Technical problems to be solved are not limited to the above-described technical problems, and other technical problems may also be present.

Technical Solution to Problem

Provided herein is an electronic device including: a display including an optical engine and a waveguide; a gaze tracking sensor; a memory configured to store one or more instructions; and a processor configured to execute the one or more instructions to: control the optical engine to output a first target image through the waveguide at preset different locations; obtain gaze information of eyes of a user corresponding to a location of the first target image by using the gaze tracking sensor; determine whether a gaze of the eyes of the user is directed to the location where the first target image is output, based on the gaze information; according to a first result of the determination, determine an impaired area of an entire visual field; and store a vision map based on the impaired area.

Also provided herein is a method of operating an electronic device, the method including: controlling an optical engine to output a first target image through a waveguide at preset different locations; obtaining gaze information of eyes of a user corresponding to a location of the first target image by using a gaze tracking sensor when the first target image is output; determining, based on the gaze information, whether a gaze of the eyes of the user is directed to the first target image; according to a first result of the determination, determining an impaired area of an entire visual field; and storing a vision map based on the impaired area.

According to another embodiment of the disclosure, a computer-readable recording medium has recorded thereon a computer program for executing the above-described method.

BRIEF DESCRIPTION OF DRAWINGS

FIG. 1B is a view for describing an embodiment of the disclosure.

MODE OF DISCLOSURE

Figure 1A:
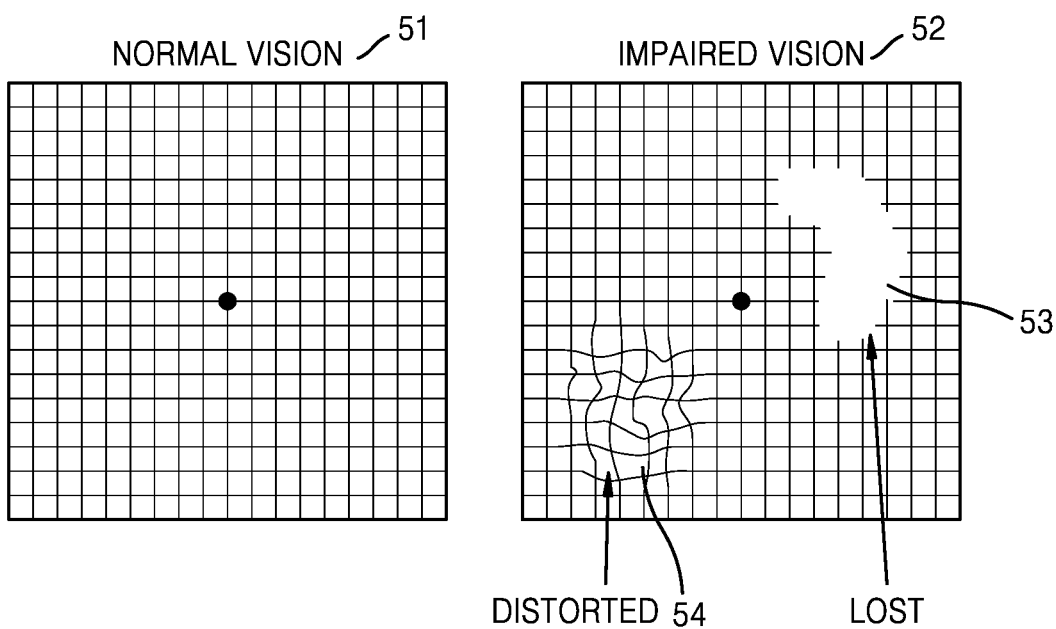
FIG. 1A is a view for describing an existing visual impairment diagnosis method.
Figure 1C:
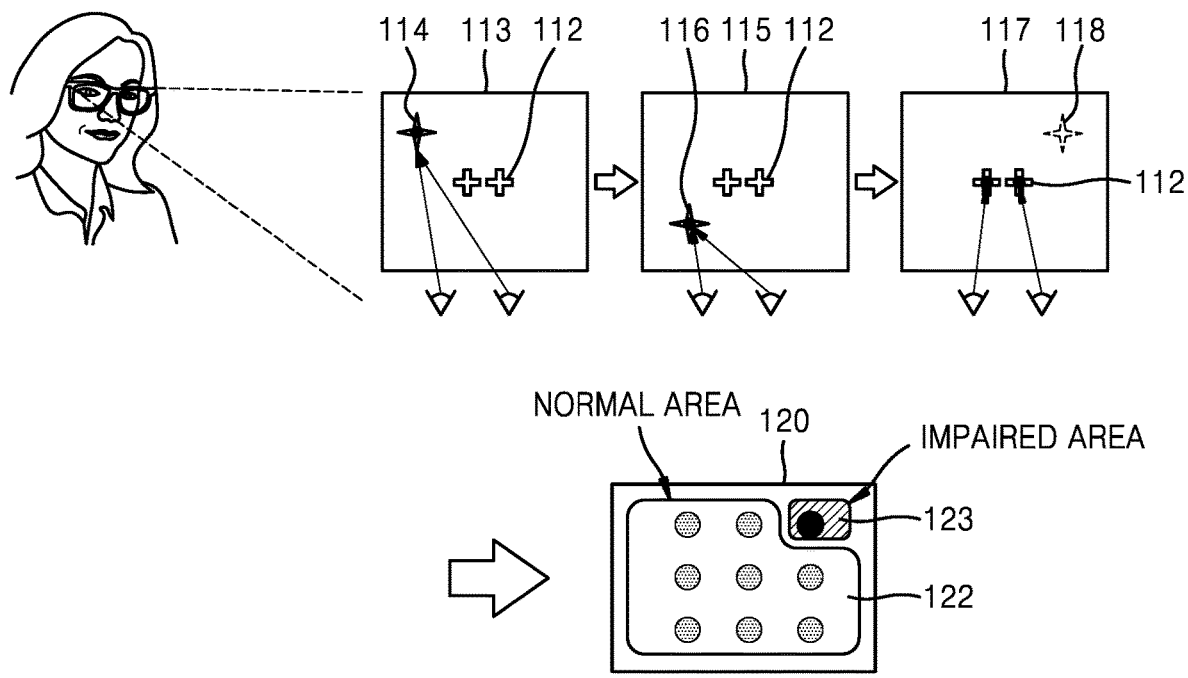
FIG. 1C is a view for describing a visual impairment diagnosis method according to an embodiment of the disclosure.

Throughout the disclosure, the expression "at least one of a, b or c" indicates only a, only b, only c, both a and b, both a and c, both b and c, all of a, b, and c, or variations thereof.

Hereinafter, the disclosure will be described in detail by explaining embodiments of the disclosure with reference to the attached drawings. The disclosure may, however, be embodied in many different forms and should not be construed as being limited to the embodiments of the disclosure set forth herein. In the drawings, parts not related to the disclosure are not illustrated for clarity of explanation, and like reference numerals denote like elements throughout.

Although the terms used herein are selected, as much as possible, from general terms that are widely used at present while taking into consideration the functions obtained in accordance with the disclosure, these terms may be replaced by other terms based on intentions of one of ordinary skill in the art, customs, emergence of new technologies, or the like. Therefore, it is noted that the terms used herein are construed based on practical meanings thereof and the whole content of this specification, rather than being simply construed based on names of the terms.

Terms such as "first" and "second" may be used to designate various elements, but the elements should not be limited by these terms. These terms are merely used to distinguish one element from another.

Terms in the following description are merely used to describe specific embodiments of the disclosure, and are not intended to limit the scope of the disclosure. The singular forms "a", "an", and "the" are intended to include the plural forms as well, unless the context clearly indicates otherwise.

Throughout the specification, when an element is referred to as being "connected to" another element, the element can be "directly connected to" the other element or be "electrically connected to" the other element via an intervening element. The terms "comprises", "comprising", "includes" and/or "including", when used herein, specify the presence of stated elements, but do not preclude the presence or addition of one or more other elements.

The definite article "the" or other demonstratives may indicate both a singular form and a plural form. Unless the context clearly indicates otherwise, operations included in a method according to an embodiment of the disclosure may be performed in an appropriate order. The order of describing the operations does not limit the scope of the disclosure.

The phrase "an embodiment of the disclosure" at various parts of this specification does not always designate the same embodiment of the disclosure.

An embodiment of the disclosure may be represented as functional blocks and various processing steps. Some or all of the functional blocks may be implemented by various numbers of hardware and/or software elements configured to perform certain functions. For example, the functional blocks of the disclosure may be implemented by one or more microprocessors or circuit elements for certain functions. As another example, the functional blocks of the disclosure may be implemented using various programming or scripting languages. The functional blocks may be implemented using algorithms executed by one or more processors. Furthermore, the disclosure might employ known technologies for electronic settings, signal processing, and/or data processing. Terms such as "mechanism", "element", "means", and "configuration" may be widely used and are not limited to mechanical and physical configurations.

In addition, connection lines or connection members between elements shown in the drawings merely illustrate examples of functional connections and/or physical or circuit connections. Connections between elements may be represented by replaceable or additional various functional connections, physical connections, or circuit connections in an actual device.

As used herein, 'augmented reality (AR)' refers to a technology for displaying a virtual image on a physical environment space of the real world or displaying a real world object and a virtual image together.

An 'AR device' is a device capable of implementing 'augmented reality', and generally includes not only AR glasses which are worn on the face of a user but also a head mounted display (HMD) or an AR helmet which is worn on the head.

A 'real scene' is a scene of the real world which is seen by the user through the AR device, and may include a real world object. A 'virtual image' is an image formed by an optical engine and may include both a still image and a moving image. The virtual image is seen together with the real scene, and may be an image including information about the real world object in the real scene, information about operation of the AR device, a control menu, or the like.

Therefore, a general AR device includes an optical engine for forming a virtual image by using light generated by a light source, and a waveguide for guiding the virtual image formed by the optical engine, to the eyes of the user, and made of a transparent material to allow a scene of the real world to be seen therethrough. As described above, because the AR device needs to allow the scene of the real world to be seen therethrough, an optical element for changing a path of light, which basically has linearity, is required to guide the light from the optical engine through waveguide to the eyes of the user. In this case, the path of light may be changed using reflection by a mirror or using diffraction by a diffractive element such as a diffractive optical element (DOE) or a holographic optical element (HOE), but is not limited thereto.

Reference will now be made in detail to embodiments of the disclosure, examples of which are illustrated in the accompanying drawings.

FIG. 1A is a view for describing an existing visual impairment diagnosis method.

As illustrated in FIG. 1A, for example, an Amsler grid test may have been used for a user to self-diagnose visual impairment. When looking at a dot in the center of the grid with one eye closed, a first grid 51 may be seen by a user with normal vision. However, a user with visual impairment due to aging of the eyes or an eye disease such as macular degeneration may see a wavy or blank area on the grid. For example, a second grid 52 may be seen by the user with an eye disease such as macular degeneration. The second grid 52 seen by the user may include a lost area 53 where the grid is not visible, and a distorted area 54 where the grid appears distorted.

For example, a preferential hyperacuity perimeter (PHP) test may have been used to diagnose visual impairment of a user. The PHP test is a test related to the ability of the user to identify misaligned lines or dots.

A user with visual impairment due to an eye disease such as macular degeneration may not recognize misaligned small dots. The PHP test is performed by presenting a plurality of aligned small dots and checking the ability of the user to recognize misaligned dots among the plurality of small dots.

In general, visual impairment due to an eye disease such as macular degeneration requires continuous monitoring of eye conditions, and self-diagnosis using specific equipment may not be easily performed by the user whereas self-diagnosis using test paper may be less accurate.

According to an embodiment of the disclosure, a user may easily and accurately self-diagnose visual impairment while using an AR device. In addition, when visual impairment is diagnosed, the AR device may provide assistance to the user to minimize inconvenience of visual impairment, while providing an AR service.

FIG. 1B is a view for describing an embodiment of the disclosure.

An electronic device 100 according to an embodiment of the disclosure may be an AR device. For example, as illustrated in FIG. 1B, the electronic device 100 may be a device implemented in the form of glasses which are wearable on the face of a user. The electronic device 100 may be a device implemented in the form of goggles, a helmet, or a hat that may be worn on the head of the user, but is not limited thereto.

As illustrated in FIG. 1B, while the user is wearing the electronic device 100 provided in the form of glasses which are wearable on the face of the user, when the electronic device 100 provides a diagnosis image including a certain pattern or dots through a display 140 (see FIG. 2) in order to diagnose visual impairment of the user, the diagnosis image may be seen like a first image 102 by a user with normal vision and be seen like a second image 104 by a user with visual impairment due to aging of the eyes or an eye disease such as macular degeneration. For example, the second image 104 seen by the user with visual impairment may include a lost area 105 which is not visible to the eyes of the user, and a distorted area 106 where a partial pattern appears distorted.

According to an embodiment of the disclosure, an entire visual field of the eyes of the user may include an entire display area on a waveguide 142 (see FIG. 2) of the electronic device 100. According to an embodiment of the disclosure, a point of the entire visual field may correspond to a point on the waveguide 142 (see FIG. 2) when a specific user wearing the electronic device 100 sees a real scene or a virtual image through the waveguide 142.

An impaired area according to an embodiment of the disclosure may refer to at least a partial area of the entire visual field which is not visible to the eyes of the user or appears distorted. The impaired area may include at least one of a lost area or a distorted area.

The lost area according to an embodiment of the disclosure may refer to at least a partial area which is not visible to the eyes of the user.

The distorted area according to an embodiment of the disclosure may refer to at least a partial area which appears distorted.

A normal area according to an embodiment of the disclosure may refer to an area excluding the impaired area from the entire visual field.

Figure 10:
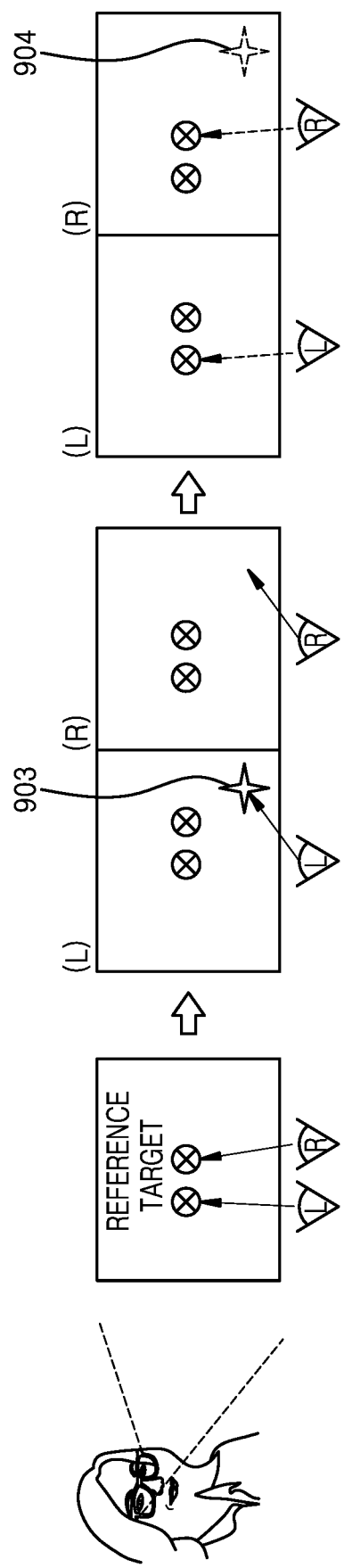
FIG. 10 is a view for describing another example in which an electronic device diagnoses visual impairment of the left or right eye, according to another embodiment of the disclosure.

FIG. 10 is a view for describing a visual impairment diagnosis method according to an embodiment of the disclosure.

According to an embodiment of the disclosure, the electronic device 100 may detect, through visual impairment diagnosis, an impaired area in an entire visual field of the eyes of a user wearing the electronic device 100.

For example, as illustrated in FIG. 10, the electronic device 100 may sequentially output diagnosis images 113, 115, and 117 in which a target image (e.g., a star-shaped dot) for attracting the eyes of the user is displayed at different locations 114, 116, and 118, and induce the user to look at the target image. When the target image is output at the different locations 114, 116, and 118, the electronic device 100 may store gaze information detected using a gaze tracking sensor 152 (see FIG. 2), in a memory 130 (see FIG. 2) in the form of a table.

The gaze information according to an embodiment of the disclosure may be information obtained by the gaze tracking sensor 152 (see FIG. 2) of the electronic device 100, and include at least one of a gaze direction of the eyes of the user, position of the pupils of the eyes of the user, or coordinates of the centers of the pupils.

Figure 2:
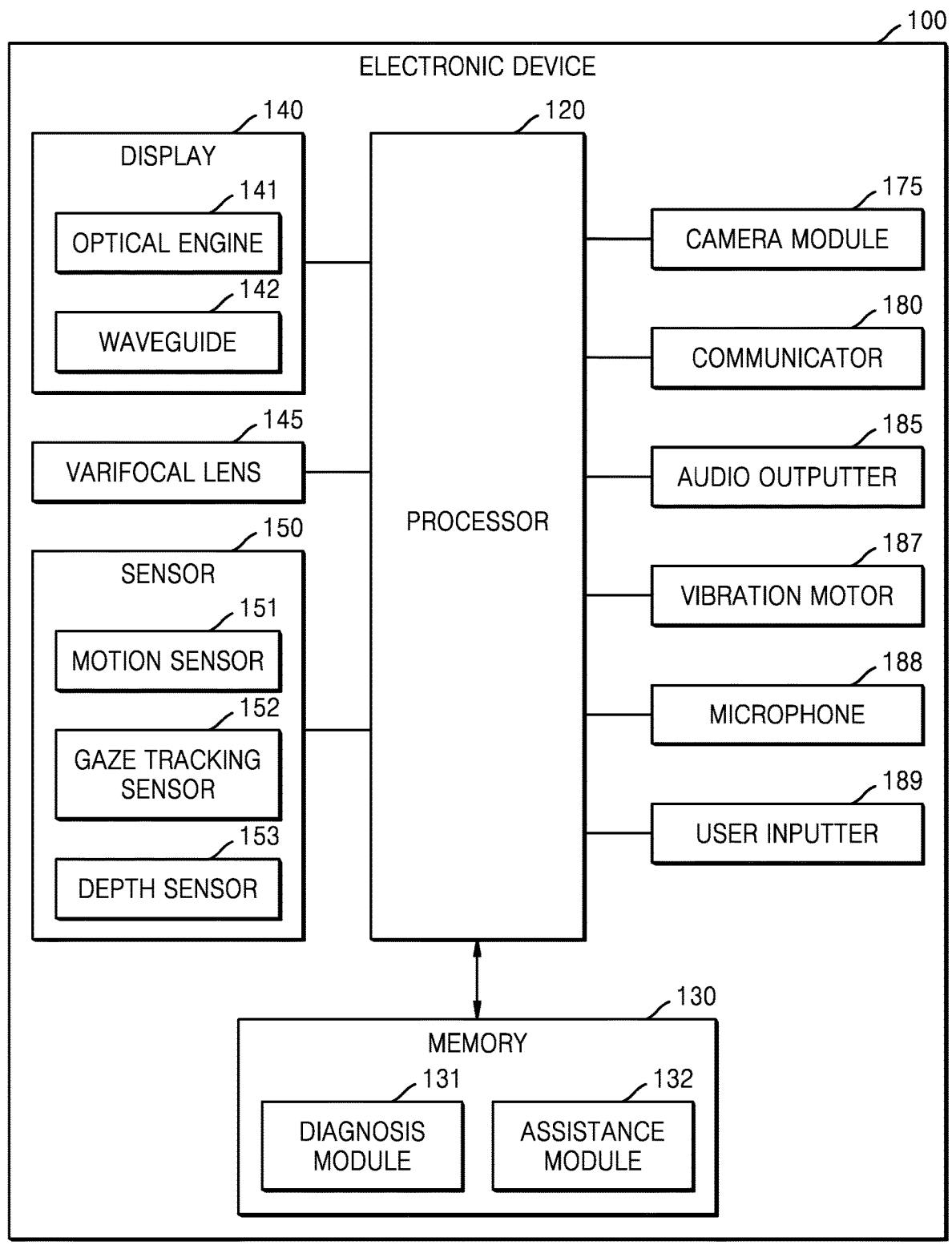
FIG. 2 is a block diagram of an electronic device according to an embodiment of the disclosure.

The electronic device 100 may determine whether a gaze of the eyes of the user is directed to a location where the target image is output, based on the gaze information obtained by the gaze tracking sensor 152 (see FIG. 2). The electronic device 100 may determine the impaired area based on the location of the output target image when the gaze of the eyes of the user is not directed to the location where the target image is output.

For example, when the electronic device 100 outputs the target image at a specific location 118 of the entire visual field, and when the gaze of the eyes of the user is not directed to a specific location 118 where the target image is output, and is directed to a default location 112, an area including the specific location 118 may be determined as the impaired area.

According to an embodiment of the disclosure, the electronic device 100 may generate a vision map by determining the impaired area of vision of the user by using the obtained gaze information, and store the vision map in the memory 130.

The vision map according to an embodiment of the disclosure may refer to data including information about locations and ranges of a normal area and an impaired area in an entire visual field of the eyes of a specific user.

For example, referring to FIG. 10, the vision map 120 may include information about locations and ranges of a normal area 122 and an impaired area 123 in the entire visual field of the user.

According to an embodiment of the disclosure, the electronic device 100 may provide a user-recognizable interface related to the impaired area not clearly visible to the user wearing the electronic device 100, by using the vision map generated through visual impairment diagnosis. For example, the electronic device 100 may display a virtual image indicating a location and range of the impaired area, in the normal area of vision of the user. The electronic device 100 may move an object included in the impaired area not visible to the user, to be displayed in the normal area of vision of the user, by using the vision map.

According to an embodiment of the disclosure, a user with visual impairment due to an eye disease such as macular degeneration may easily diagnose visual impairment and continuously monitor impairment by using the electronic device 100 without using additional equipment.

In addition, according to an embodiment of the disclosure, the electronic device 100 may provide a user-specific AR service on the basis of previously obtained visual impairment information of the user. The electronic device 100 may provide assistance to the user to recognize the impaired area and to see an object, which is located in the impaired area and thus is not accurately visible to the user, in the normal area, thereby minimizing inconvenience caused by visual impairment.

A method, performed by the electronic device 100, of diagnosing visual impairment of the eyes of the user, a method, performed by the electronic device 100, of providing assistance to the user with visual impairment, and examples thereof will be described below with reference to the drawings.

FIG. 2 is a block diagram of the electronic device 100 according to an embodiment of the disclosure.

According to an embodiment of the disclosure, the electronic device 100 may be an AR device including a communication function and a data processing function to provide AR images, but is not limited thereto.

Referring to FIG. 2, the electronic device 100 according to an embodiment of the disclosure may include the memory 130, a processor 120, the display 140, a varifocal lens 145, a sensor 150, a camera module 175, a communicator 180, an audio outputter 185, a vibration motor 187, a microphone 188, an a user inputter 189. However, not all elements illustrated in FIG. 2 are essential elements of the electronic device 100. The electronic device 100 may be implemented with more or fewer elements than the elements illustrated in FIG. 2.

The processor 120 of the electronic device 100 may execute programs stored in the memory 130 to control the display 140, the varifocal lens 145, the sensor 150, the camera module 175, the communicator 180, the audio outputter 185, the vibration motor 187, the microphone 188, and the user inputter 189.

The memory 130 according to an embodiment of the disclosure may store the programs to be executed by the processor 120, and store data input to or to be output from the electronic device 100.

The memory 130 may include at least one type of storage medium among flash memory, a hard disk, a multimedia card micro, a memory card (e.g., a secure digital (SD) or extreme digital (XD) memory card), random access memory (RAM), static random access memory (SRAM), read-only memory (ROM), electrically erasable programmable read-only memory (EEPROM), programmable read-only memory (PROM), magnetic memory, a magnetic disc, and an optical disc.

The programs stored in the memory 130 may be classified into a plurality of software modules, for example, a diagnosis module 131 and an assistance module 132, depending on functions thereof, but are not limited thereto and may include only some of the above-mentioned software modules or further include other software modules.

The processor 120 controls overall operations of the electronic device 100. The processor 120 may execute instructions or programs stored in the memory 130 to control operations or functions performed by the electronic device 100.

According to an embodiment of the disclosure, the processor 120 may include one or more processors. The processor 120 may include at least one type of hardware among, for example, a central processing unit (CPU), a microprocessor, a graphics processing unit (GPU), an application-specific integrated circuit (ASIC), a digital signal processor (DSP), a digital signal processing device (DSPD), a programmable logic device (PLD), and a field programmable gate array (FPGA), but is not limited thereto.

The processor 120 may execute the diagnosis module 131 stored in the memory 130 to detect an impaired area of vision of a user.

In order to detect the impaired area of vision of the user, the processor 120 may control an optical engine 141 to output a diagnosis image including a target image through the waveguide 142.

According to an embodiment of the disclosure, the diagnosis image may include the target image configured as a certain-shaped dot or a certain pattern. For example, the certain-shaped dot includes a star-shaped, X-shaped, or plus-shaped dot, but is not limited thereto. The certain pattern includes a plurality of dots aligned at certain intervals, an arbitrary closed curve, or a wave pattern, but is not limited thereto.

According to an embodiment of the disclosure, the impaired area may include at least one of a lost area or a distorted area.

According to an embodiment of the disclosure, in order to detect the lost area, the processor 120 may use a diagnosis image including a first target image configured as a certain-shaped dot.

The processor 120 may control the optical engine 141 to output the first target image through the waveguide 142 sequentially at preset different locations of an entire visual field of the eyes of the user at preset time intervals.

According to an embodiment of the disclosure, the preset different locations may include at least one of a plurality of locations spaced apart from each other at certain intervals on the waveguide 142.

The processor 120 may output, through the audio outputter 185, guidance sound for instructing the user wearing the electronic device 100 to look at the first target image displayed through the waveguide 142.

The processor 120 may obtain gaze information of the eyes of the user corresponding to a location of the output first target image by using the gaze tracking sensor 152 when the first target image is output sequentially at the preset different locations. The processor 120 may determine whether a gaze direction of the eyes of the user converges on the location where the first target image is output, based on the obtained gaze information. According to a result of the determination, the processor 120 may determine an impaired area of the entire visual field based on the location of the output first target image.

When vision of the eyes of the user includes a lost area, and when the target image is displayed at a location corresponding to the lost area in the entire visual field, the eyes of the user may not recognize the target image and thus a gaze of the eyes of the user will not be directed to the location where the target image is displayed.

While the first target image (e.g., a star-shaped dot) is being output sequentially at the preset different locations, the processor 120 may determine a certain area including the location where the first target image is output when the gaze direction of the eyes of the user does not converge on the location where the first target image is output, as the lost area.

The processor 120 may generate a vision map related to the impaired area, and a normal area excluding the impaired area from the entire visual field, based on the impaired area including the determined lost area, and store the vision map in the memory 130.

Figure 3A:
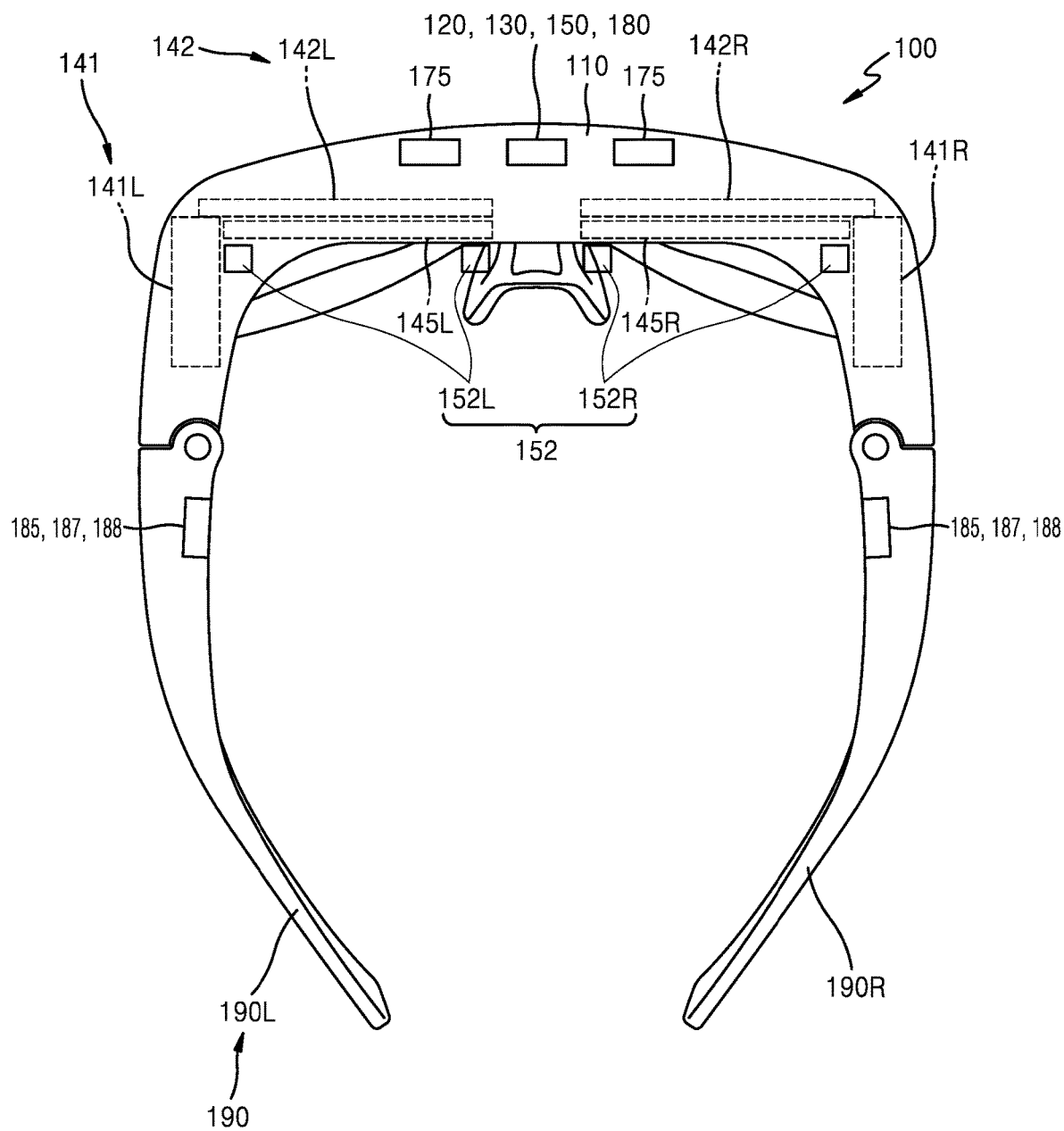
FIG. 3A is a view showing an example of an electronic device according to an embodiment of the disclosure.

In order to detect the lost area of each of the left and right eyes of the user, the processor 120 may provide the same diagnosis image including the target image sequentially to a left-eye waveguide 142L (see FIG. 3A) and a right-eye waveguide 142R (see FIG. 3A). The processor 120 may determine that the user may not recognize the diagnosis image provided on the left-eye waveguide 142L (see FIG. 3A) or the right-eye waveguide 142R (see FIG. 3A), and determine visual impairment of the left or right eye of the user.

According to an embodiment of the disclosure, in order to detect the distorted area, the processor 120 may use a diagnosis image including a second target image configured as a certain pattern.

The processor 120 may control the optical engine 141 to output the second target image through the waveguide 142. For example, the processor 120 may output a plurality of dots aligned in a certain pattern sequentially at preset different locations of the entire visual field. The preset different locations may include at least one of a plurality of locations spaced apart from each other at certain intervals on the waveguide 142.

For example, the processor 120 may output an arbitrary closed curve including a wave pattern by gradually reducing the size thereof from the periphery to the center of vision of the user.

According to an embodiment of the disclosure, the processor 120 may output, through the audio outputter 185, guidance information related to the second target image. For example, the processor 120 may output sound for instructing to trace the pattern of the second target image configured as a dashed line with a finger.

According to an embodiment of the disclosure, the processor 120 may obtain a gesture input of the user by using a depth sensor 153. For example, the processor 120 may obtain a gesture input of the user wearing the electronic device 100 for tracing a pattern of alignment of the plurality of dots output on the waveguide 142 with a finger while looking at the plurality of dots.

The processor 120 may obtain a user input pattern based on the obtained gesture input of the user.

The processor 120 may compare the second target image configured as the certain pattern to the obtained user input pattern. The processor 120 may determine the distorted area based on a location of the output second target image according to a result of the comparison.

When vision of the eyes of the user includes a distorted area, and when the certain pattern, e.g., the target image in which the plurality of dots are aligned, is displayed at a location corresponding to the distorted area of the entire visual field, the pattern in which the plurality of dots are aligned may appear distorted and thus the user input pattern may not match the pattern of the target image.

The processor 120 may determine an area where the second target image does not match the obtained user input pattern, and determine the distorted area based on the area where the second target image does not match the user input pattern.

The processor 120 may generate a vision map related to the impaired area, and a normal area excluding the impaired area from the entire visual field, based on the impaired area including the determined distorted area, and store the vision map in the memory 130.

The processor 120 may compare the second target image configured as the certain pattern to the obtained user input pattern, and calculate a degree of distortion in the distorted area, based on a distance between the second target image and the obtained user input pattern.

In order to detect the distorted area of each of the left and right eyes of the user, the processor 120 may provide the diagnosis image including the target image on any one of the left-eye waveguide 142L (see FIG. 3A) and the right-eye waveguide 142R (see FIG. 3A). The processor 120 may determine that the user may not accurately recognize the diagnosis image provided on the left-eye waveguide 142L (see FIG. 3A) or the right-eye waveguide 142R (see FIG. 3A), and determine visual impairment of the left or right eye of the user.

The processor 120 may execute the assistance module 132 stored in the memory 130 to provide assistance to the user to recognize the impaired area.

According to an embodiment of the disclosure, the processor 120 may control the optical engine 141 to output a guidance image for notifying the user of the impaired area through the waveguide 142, based on the previously generated vision map.

For example, the processor 120 may display a virtual guidance image indicating the impaired area of vision of the user, in the normal area adjacent to the impaired area of vision of the user.

As such, when the user sees a real scene through the waveguide 142, the user may recognize that a real world object of the real scene, which is located in a direction and at a distance where a guidance image is displayed, is not accurately visible due to visual impairment of the user. In addition, according to an embodiment of the disclosure, the processor 120 may control an object included in the impaired area to be displayed in the normal area of vision of the user by using a prism mode of the varifocal lens 145 such that the user may recognize the object included in the impaired area.

According to an embodiment of the disclosure, when the user wearing the electronic device 100 sees a real scene through the waveguide 142, the processor 120 may detect an object included in the impaired area on an entire display area of the waveguide 142, based on the previously generated vision map. The processor 120 may capture an image of a real scene in front of the electronic device 100 by using the camera module 175, and perform object recognition on the captured image by using a certain object recognition algorithm. The processor 120 may detect an object included in an area of the captured image corresponding to the impaired area of vision of the user. The processor 120 may detect a depth of at least one real world object included in the real scene in front of the electronic device 100 by using the depth sensor 153. The processor 120 may detect the object included in the area corresponding to the impaired area of vision of the user, based on the detected depth of the at least one real world object.

The processor 120 may apply the prism mode to a specific area of the varifocal lens 145 corresponding to the impaired area, in such a manner that the detected object is displayed in the normal area of vision of the user.

According to an embodiment of the disclosure, the prism mode is a mode in which refractive power of the specific area of the varifocal lens 145 is changed. The refractive power of the varifocal lens 145 may be changed by changing orientation of liquid crystal (LC) molecules in the varifocal lens 145.

When the prism mode is applied to the varifocal lens 145, orientation of the LC molecules may be changed by applying a voltage to the specific area of the varifocal lens 145 corresponding to the impaired area of vision of the user to have a phase profile corresponding to the prism mode, and thus the refractive power may be changed. As such, a path of light passing through the specific area of the varifocal lens 145 may be changed.

The processor 120 may exert control to move an image of the object included in the impaired area to a location corresponding to the normal area of vision of the user, by applying the prism mode to the specific area of the varifocal lens 145 corresponding to the impaired area.

As such, when the user wearing the electronic device 100 sees the real scene, the user may recognize the object, which is included in the impaired area of vision of the user and thus is not visible to the user, at another location.

The display 140 may output information processed by the processor 120. For example, the display 140 may display a virtual object.

According to an embodiment of the disclosure, the display 140 may provide an AR image. The display 140 according to an embodiment of the disclosure may include the waveguide 142 and the optical engine 141.

The waveguide 142 may be made of a transparent material, and a partial area of a rear surface thereof may available for view by the user when the electronic device 100 is worn. The waveguide 142 may be configured as a transparent monolayer or multilayer flat panel capable of reflecting and propagating light therein. The waveguide 142 may face an exit surface of the optical engine 141 to receive light of a virtual image projected from the optical engine 141. Herein, the transparent material refers to a material through which light may pass, and may or may not have a transparency of 100% and may have a certain color.

In an embodiment of the disclosure, because the waveguide 142 is made of a transparent material, the user may see not only a virtual object of a virtual image but also an external real scene through the display 140, and thus the waveguide 142 may also be called a see-through display. The display 140 may provide an AR image by outputting a virtual object of a virtual image through the waveguide 142.

The varifocal lens 145 may be mounted in the electronic device 100 to provide assistance to the user with visual impairment. The varifocal lens 145 may be aligned to overlap with the waveguide 142 to face the eyes of the user. The varifocal lens 145 may be generally implemented as a liquid lens or an LC lens. For example, the varifocal lens 145 may be implemented as a liquid lens in which a transparent fluid is surrounded by a flexible plastic membrane. The fluid in the varifocal lens 145 may move according to an electrical signal applied to the varifocal lens 145, and thus refractive power of the varifocal lens 145 may be changed. As another example, the varifocal lens 145 may be implemented as an LC lens in which a transparent electrode is provided on both surfaces of a transparent LC layer. Orientation of liquid crystals in the LC layer may be changed according to an electrical signal applied to the transparent electrode, and thus a path of light passing through the LC lens may be changed and the refractive power of the varifocal lens 145 may be changed.

For example, an electrical signal or voltage value to be applied to an electrode may be preset in such a manner that the refractive power of the varifocal lens 145 corresponds to a diopter value (e.g., . . . −3D, −2D, −1D, 0, 1D, 2D, 3D . . . ), and refractive power of a corresponding diopter value may be applied to the varifocal lens 145 when an electrical signal or voltage is applied to the electrode. However, the refractive power of the varifocal lens 145 is not limited thereto and, for example, the electrical signal or voltage value to be applied to the electrode may be preset in such a manner that the refractive power of the varifocal lens 145 may be changed to successive values.

According to an embodiment of the disclosure, a prism mode may be applied to a specific area of the varifocal lens 145. The prism mode is a mode in which refractive power of the specific area of the varifocal lens 145 is changed. The refractive power of the varifocal lens 145 may be changed by changing orientation of LC molecules in the varifocal lens 145.

According to an embodiment of the disclosure, when the prism mode is applied to the varifocal lens 145, orientation of the LC molecules may be changed by applying a voltage to the specific area of the varifocal lens 145 to have a phase profile corresponding to the prism mode, and thus the refractive power may be changed. As such, a path of light passing through the specific area of the varifocal lens 145 may be changed.

According to an embodiment of the disclosure, the prism mode may be applied to the specific area of the varifocal lens 145 corresponding to the impaired area of vision of the user. By changing the path of light passing through the specific area of the varifocal lens 145 to which the prism mode is applied, an image of a real world object included in the impaired area may be displayed in the normal area of vision of the user. In general, a prism may cause dispersion of light by diffraction (see the illustration on the right hand side of FIG. 5). In some embodiments, the varifocal lens 145 in prism mode disperses light of the real world object away from the impaired area and into the normal area of vision. The user thus obtains information of the real world object.

When the electronic device 100 is a glass-type device, the varifocal lens 145 may include a left-eye varifocal lens and a right-eye varifocal lens.

The sensor 150 may include a motion sensor 151, the gaze tracking sensor 152, and the depth sensor 153.

The motion sensor 151 may be an inertial measurement unit (IMU). The IMU may be a combination of sensors configured to detect motion, i.e., changes in position and orientation, of an object in the 3-dimensional space. For example, the combination of sensors may include an accelerometer, an angular speedometer, a magnetometer, and a gyroscope.

The motion sensor 151 may include at least one of an acceleration sensor, a magnetic sensor, or a gyroscope sensor.

According to an embodiment of the disclosure, when the user wearing the electronic device 100 moves the head according to the pattern of the target image included in the diagnosis image for diagnosing visual impairment of the user, the motion sensor 151 may sense a head motion pattern of the user.

The gaze tracking sensor 152 may detect gaze information of the eyes of the user. According to an embodiment of the disclosure, the gaze information may include at least one of a gaze direction of the eyes of the user, position of the pupils of the eyes of the user, or coordinates of the centers of the pupils.

The gaze tracking sensor 152 may provide light to the eyes (e.g., the left or right eye) of the user and sense the amount of light reflected from the eyes of the user. The gaze tracking sensor 152 may detect the gaze direction of the eyes of the user, the position of the pupils of the eyes of the user, or the coordinates of the centers of the pupils, based on the sensed amount of light.

Alternatively, the gaze tracking sensor 152 may provide light to the eyes of the user and capture an image of the eyes of the user. The gaze tracking sensor 152 may detect the gaze direction of the eyes of the user, the position of the pupils of the eyes of the user, or the coordinates of the centers of the pupils, based on the captured image of the eyes of the user.

The depth sensor 153 may obtain depth information of one or more objects included in the real world. The depth information may correspond to a distance from the depth sensor 153 to a specific object. The depth value may increase in proportion to the distance from the depth sensor 153 according to an embodiment of the disclosure to the specific object.

The depth sensor 153 according to an embodiment of the disclosure may obtain the depth information of the objects in various manners. For example, the depth sensor 153 may obtain the depth information by using at least one of a time of flight (TOF) method, a structured light method, or a stereo image method. The depth sensor 153 using the stereo image method generally includes two or more cameras.

According to an embodiment of the disclosure, the depth sensor 153 may sense depth information of a real world object included in a real scene seen through the waveguide 142 by the user wearing the electronic device 100. The processor 120 may obtain information indicating whether the real world object is present in front of the electronic device 100, a direction and distance of the real world object, etc., based on the depth information of the real world object sensed by the depth sensor 153.

The depth sensor 153 may also sense depth information of fingers of the user wearing the electronic device 100. The processor 120 may obtain a gesture input of a hand of the user by recognizing a shape or a motion pattern of the hand of the user, based on the depth information of the fingers sensed by the depth sensor 153.

The camera module 175 may capture an image of an ambient environment of the electronic device 100. The camera module 175 may obtain still images or video frames by using an image sensor when an application requiring an image capture function is executed.

The images captured using the image sensor may be processed by the processor 120 or a separate image processor (not shown). The captured images may be displayed through the display 140.

The images processed by the processor 120 or the separate image processor (not shown) may be stored in the memory 130 or transmitted through the communicator 180 to an external device. Two or more camera modules 175 may be provided depending on the configuration of the electronic device 100.

The communicator 180 may include one or more elements for enabling communication between the electronic device 100 and an external server (not shown) or an external device (not shown).

For example, the communicator 180 may include a short-range wireless communicator and a mobile communicator.

The short-range wireless communicator may include a Bluetooth communicator, a near-field communication (NFC)/radio-frequency identification (RFID) communicator, a wireless local area network (WLAN) (or Wi-Fi) communicator, a Zigbee communicator, an infrared data association (IrDA) communicator, a Wi-Fi direct (WFD) communicator, a ultra-wideband (UWB) communicator, or an Ant+ communicator, but is not limited thereto.

The mobile communicator transmits and receives wireless signals to and from at least one of a base station, an external device, or a server in a mobile communication network. Herein, the wireless signals may include various types of data related to transmission and reception of voice call signals, video call signals, or text/multimedia messages.

The audio outputter 185 outputs audio data received from the communicator 180 or stored in the memory 130. The audio outputter 185 outputs an audio signal related to a function performed by the electronic device 100 (e.g., call signal reception sound, message reception sound, or notification sound).

The audio outputter 185 according to an embodiment of the disclosure may include a speaker or a buzzer. The audio outputter 185 according to an embodiment of the disclosure may be implemented in the form of earphones mounted on or detachable from the electronic device 100. The audio outputter 185 according to an embodiment of the disclosure may output audio data in a bone conduction manner.

The audio outputter 185 according to an embodiment of the disclosure may output guidance information for instructing the user wearing the electronic device 100 to look at the target image displayed through the waveguide 142. The audio outputter 185 may output guidance information for instructing the user wearing the electronic device 100 to trace the pattern of the target image displayed through the waveguide 142 with a finger, but is not limited thereto.

The vibration motor 187 may output a vibration signal. For example, the vibration motor 187 may output a vibration signal corresponding to output of audio or video data (e.g., call signal reception sound or message reception sound). The vibration motor 187 may output a vibration signal when a user input is received from the user inputter 189. The vibration motor 187 may provide a notification with vibration when the electronic device 100 operates in a vibration mode.

The microphone 188 receives an external audio signal and processes the audio signal into electrical voice data. For example, the microphone 188 may receive the audio signal from an external device or user. The microphone 188 may receive a voice input of the user for controlling the electronic device 100. The microphone 188 may use various noise cancellation algorithms to cancel noise added while receiving an external audio signal.

The user inputter 189 refers to a means by which a user inputs data for controlling the electronic device 100. For example, the user inputter 189 may include at least one of a keypad, a dome switch, a touchpad (e.g., a capacitive overlay, resistive overlay, infrared beam, surface acoustic wave, integral strain gauge, or piezoelectric touchpad), a jog wheel, or a jog switch, but is not limited thereto.

FIG. 3A is a view showing an example of the electronic device 100 according to an embodiment of the disclosure.

FIG. 3A is a view showing an example of an AR device including the varifocal lens 145, according to an embodiment of the disclosure. The electronic device 100 of FIG. 2 may be implemented as, for example, a glass-type display device including a glass-type body wearable by a user as illustrated in FIG. 3A and indicated with item number 100, but is not limited thereto.

The glass-type body may include a frame 110 and glass legs 190. The glass legs 190 may include a left leg 190L and a right leg 190R, and be connected to both end pieces of the frame 110.

The varifocal lens 145 and the waveguide 142 may be provided on the frame 110. The varifocal lens 145 may include a left-eye varifocal lens 145L and a right-eye varifocal lens 145R. The waveguide 142 may be configured to receive projected light input to an input area and output at least a part of the input light from an output area. The waveguide 142 may include the left-eye waveguide 142L and the right-eye waveguide 142R.

The left-eye varifocal lens 145L and the left-eye waveguide 142L may be provided at a location corresponding to the left eye of the user, and the right-eye varifocal lens 145R and the right-eye waveguide 142R may be provided at a location corresponding to the right eye of the user. For example, the left-eye varifocal lens 145L and the left-eye waveguide 142L, or the right-eye varifocal lens 145R and the right-eye waveguide 142R may be attached to each other, but are not limited thereto.

The optical engine 141 including a projector that projects light containing an image may include a left-eye optical engine 141L and a right-eye optical engine 141R. The left-eye optical engine 141L and the right-eye optical engine 141R may be located at both end pieces of the frame 110. Light emitted from the optical engine 141 may be displayed through the waveguide 142.

The electronic device 100 may include the gaze tracking sensor 152 to track a gaze of the user. The gaze tracking sensor 152 according to an embodiment of the disclosure may include a first gaze tracking sensor 152L for tracking a gaze of the left eye of the user, and a second gaze tracking sensor 152R for tracking a gaze of the right eye of the user.

Two example camera modules 175 are indicated in FIG. 3A. Also, processor 120, memory 130, sensor 150, communicator 180, audio outputter 185, vibration motor 187 and microphone 188 are indicated in FIG. 3A (these items do not need to be co-located in electronic device 100). The camera modules 175 may be located for capture of good-quality images for stereo processing. The processor 120, memory 130, sensor 150, communicator 180, audio outputter 185, vibration motor 187 and microphone 188 may be configured and located in, on or with electronic device 100 based on manufacturing, ergonomic and cost factors.

Figure 3B:
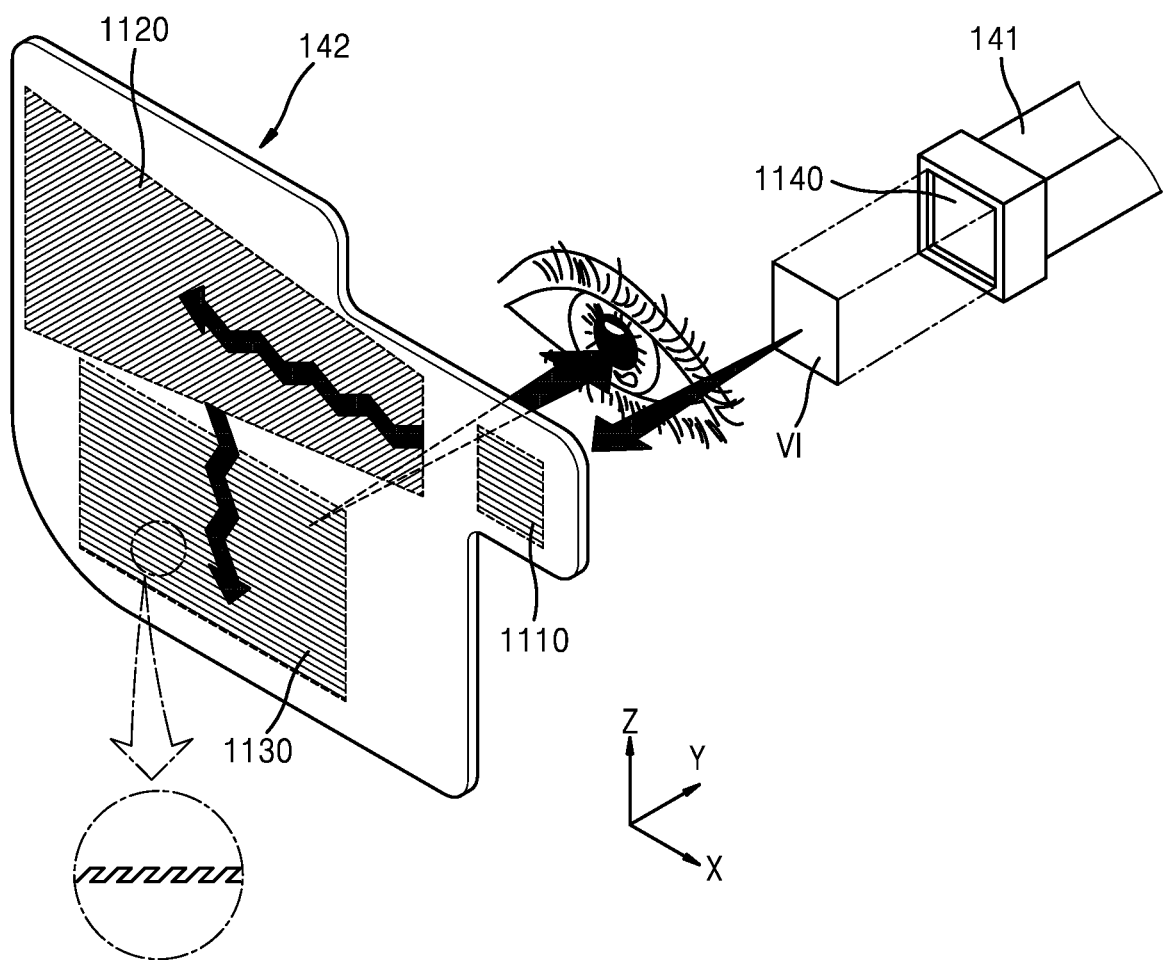
FIG. 3B is a view for describing an optical engine and a waveguide, according to an embodiment of the disclosure.

FIG. 3B is a view for describing the optical engine 141 and the waveguide 142, according to an embodiment of the disclosure.

The optical engine 141 may be configured to generate light of a virtual image, and include, for example, an image panel and a projector including a projection optical system.

The optical engine 141 may include a light source for outputting light, an image panel for forming a 2-dimensional virtual image by using the light output from the light source, and a projection optical system for projecting light of the virtual image formed on the image panel. The light source may be an optical part for emitting light, and generate light by adjusting RGB colors. The light source may be configured as, for example, a light-emitting diode (LED). The image panel may be configured as a reflective image panel for modulating and reflecting the light emitted from the light source into light containing a 2-dimensional image. The reflective image panel may be, for example, a digital micromirror device (DMD) panel, a liquid crystal on silicon (LCoS) panel, or another known reflective image panel. The projection optical system may be an element for projecting the light containing the image and reflected by the image panel, onto the waveguide 142, and include one or more projection lenses.

The optical engine 141 may obtain image data configuring a virtual image from the processor 120, generate a virtual image based on the obtained image data, and project the light configuring the virtual image and output from the light source, through an exit surface 1140 onto the waveguide 142. The processor 120 may provide image data including RGB color values and brightness values of a plurality of pixels configuring a virtual image to the optical engine 141, and the optical engine 141 may project light configuring the virtual image onto the waveguide 142 by controlling the light source according to the RGB color values and the brightness values of the plurality of pixels. The optical engine 141 may project the virtual image by using a transmissive projection technology where a light source is modulated by an optically active material and backlit with white light.

The waveguide 142 may be made of a transparent material, and a partial area of a rear surface thereof may be available for view by a user when the electronic device 100 is worn. The rear surface of the waveguide 142 refers to a surface facing the eyes of the user when the electronic device 100 is worn, and a front surface of the waveguide 142 refers to a surface opposite to the rear surface (i.e., a surface away from the eyes of the user).

According to an embodiment of the disclosure, the waveguide 142 may be configured as a transparent monolayer or multilayer flat panel capable of reflecting and propagating light therein. The waveguide 142 may include a first area 1110 facing the exit surface 1140 of the optical engine 141 to receive light configuring a projected virtual image VI, a second area 1120 for propagating the light configuring the virtual image VI and incident on the first area 1110, and a third area 1130 for outputting the light of the virtual image VI propagated in the second area 1120, toward the eyes of the user.

Each of the first area 1110, the second area 1120, and the third area 1130 may include a diffraction grating for changing a path of the light configuring the virtual image VI. The waveguide 142 may guide light by changing a propagation path of the light of the virtual image VI by using the diffraction gratings on the first area 1110, the second area 1120, and the third area 1130, and ultimately outputting reflected light of the virtual image VI from the third area 1130 to the eyes of the user.

Figure 4A:
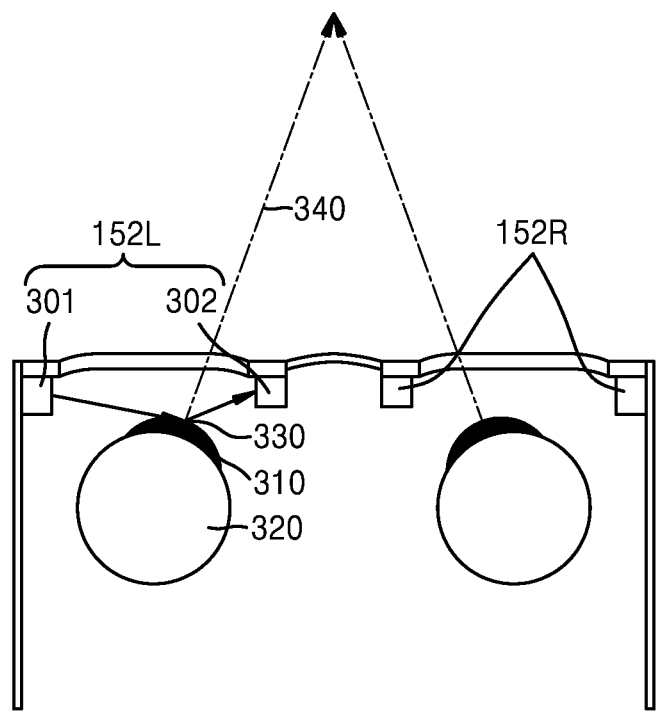
FIG. 4A is a view for describing a method of operating a gaze tracking sensor, according to an embodiment of the disclosure.

FIG. 4A is a view for describing a method of operating the gaze tracking sensor 152, according to an embodiment of the disclosure.

FIG. 4A is a view for describing a method of tracking a gaze of a user based on the amount of light reflected from the eyes of the user.

Because the first gaze tracking sensor 152L and the second gaze tracking sensor 152R according to an embodiment of the disclosure have the same structure and operate in the same manner, the first gaze tracking sensor 152L will be representatively described in relation to FIG. 4A.

Referring to FIG. 4A, the first gaze tracking sensor 152L according to an embodiment of the disclosure may include a light emitter 301 for providing light to an eye of the user, and a sensor 302 for sensing light. The light emitter 301 may include a light source for providing light, and a scanning mirror for controlling the direction of the light provided from the light source. The scanning mirror may control the light provided from the light source to proceed toward an eye 320 (e.g., a cornea 310) of the user wearing the electronic device 100. The scanning mirror may include a structure capable of mechanically changing a reflection angle to reflect the light provided from the light source toward the eye 320 of the user, and scan an area including the cornea 310 by using the light provided from the light source according to the changed reflection angle.

The sensor 302 may sense light reflected from the eye 320 of the user, and measure the amount of the sensed light. For example, when light is reflected from the center of the cornea 310 of the user, the amount of the light sensed by the sensor 302 may be the highest. As such, the first gaze tracking sensor 152L may determine a gaze direction 340 of the eye of the user based on a point where the light is incident on and reflected from the eye of the user when the amount of the light sensed by the sensor 302 is the highest. For example, the first gaze tracking sensor 152L may determine the direction 340 of a virtual line connecting the center of the eye 320 of the user to a point 330 where the light is incident on and reflected from the eye of the user when the amount of the light is the highest, as a gaze direction of the eye of the user (e.g., the left eye of the user). However, the gaze direction determination method is not limited thereto.

The second gaze tracking sensor 152R may also determine a gaze direction of an eye (e.g., the right eye) of the user in the same manner as that described above in relation to FIG. 4A.

Figure 4B:
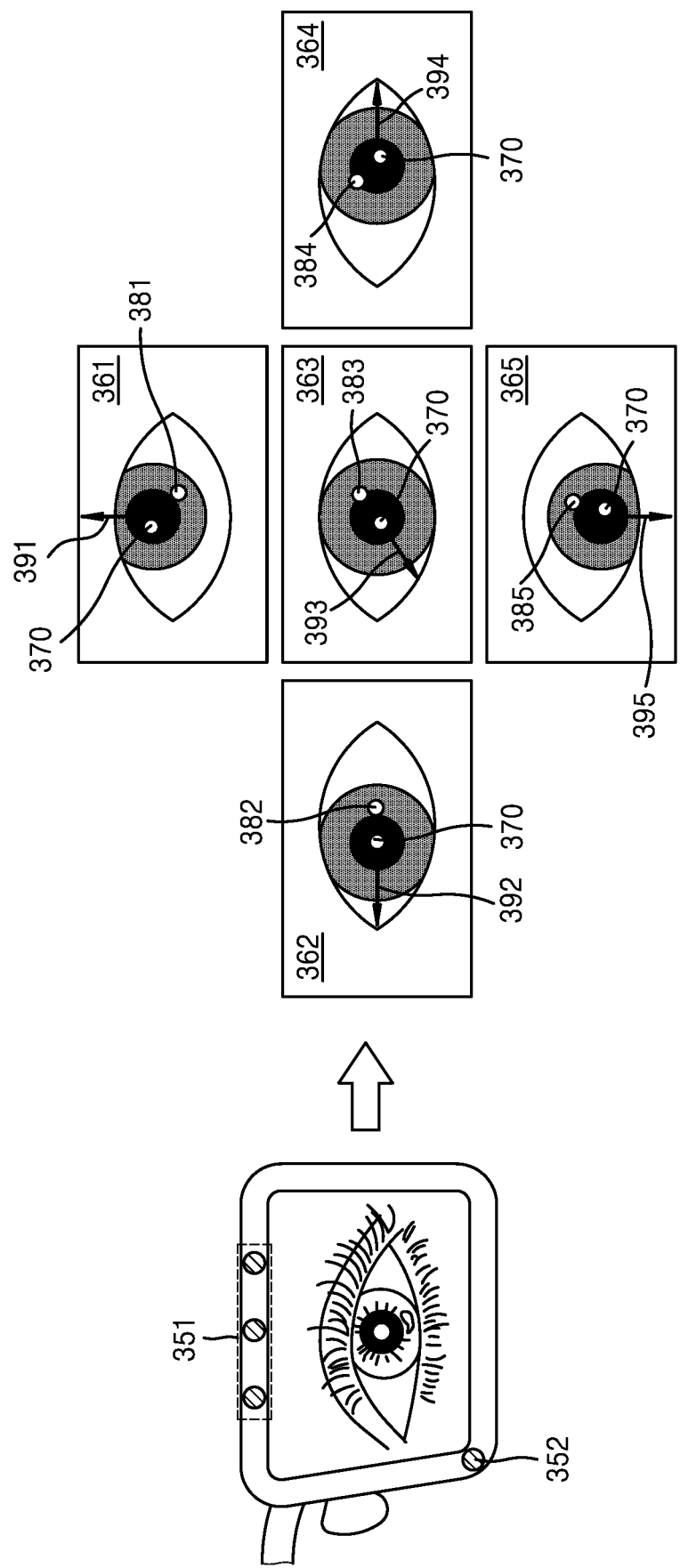
FIG. 4B is a view for describing a method of operating a gaze tracking sensor, according to another embodiment of the disclosure.

FIG. 4B is a view for describing a method of operating the gaze tracking sensor 152, according to another embodiment of the disclosure. The first gaze tracking sensor 152L according to another embodiment of the disclosure may include a light emitter 351 and an image capturer 352.

FIG. 4B is a view for describing a method of tracking a gaze of a user based on a position of light reflected from an eye of the user.

The light emitter 351 according to an embodiment of the disclosure may include, for example, an infrared light-emitting diode (IR LED). As illustrated in FIG. 4B, the light emitter 351 may include a plurality of LEDs provided at different locations. The light emitter 351 may provide light (e.g., infrared light) to an eye of the user to capture an image of the eye of the user. When the light is provided to the eye of the user, the light may be reflected on the eye of the user.

The image capturer 352 may include at least one camera and, in this case, the at least one camera may include an infrared (IR) camera. The electronic device 100 may track a gaze of the eye of the user (e.g., the left eye of the user) by using an eye image of the user captured by the image capturer 352. For example, the first gaze tracking sensor 152L may track the gaze of the user by detecting a pupil and reflected light in the eye image of the user. The first gaze tracking sensor 152L may detect positions of the pupil and the reflected light in the eye image of the user, and determine a gaze direction of the eye of the user based on the relationship between the position of the pupil and the position of the reflected light.

For example, the first gaze tracking sensor 152L may detect a pupil 370 and reflected light 381 in a captured first eye image 361, and determine a gaze direction 391 of the eye of the user based on the relationship between a position of the pupil 370 and a position of the reflected light 381. In the same manner, the first gaze tracking sensor 152L may detect the pupil 370 and reflected light 382, 383, 384, or 385 in each of second to fifth eye images 362, 363, 364, and 365, and determine a gaze direction 392, 393, 394, or 395 of the eye of the user based on the relationship between a position of the pupil 370 and a position of the reflected light 382, 383, 384, or 385.

The second gaze tracking sensor 152R may also determine a gaze direction of an eye (e.g., the right eye) of the user in the same manner as that described above in relation to FIG. 4B.

Figure 5:
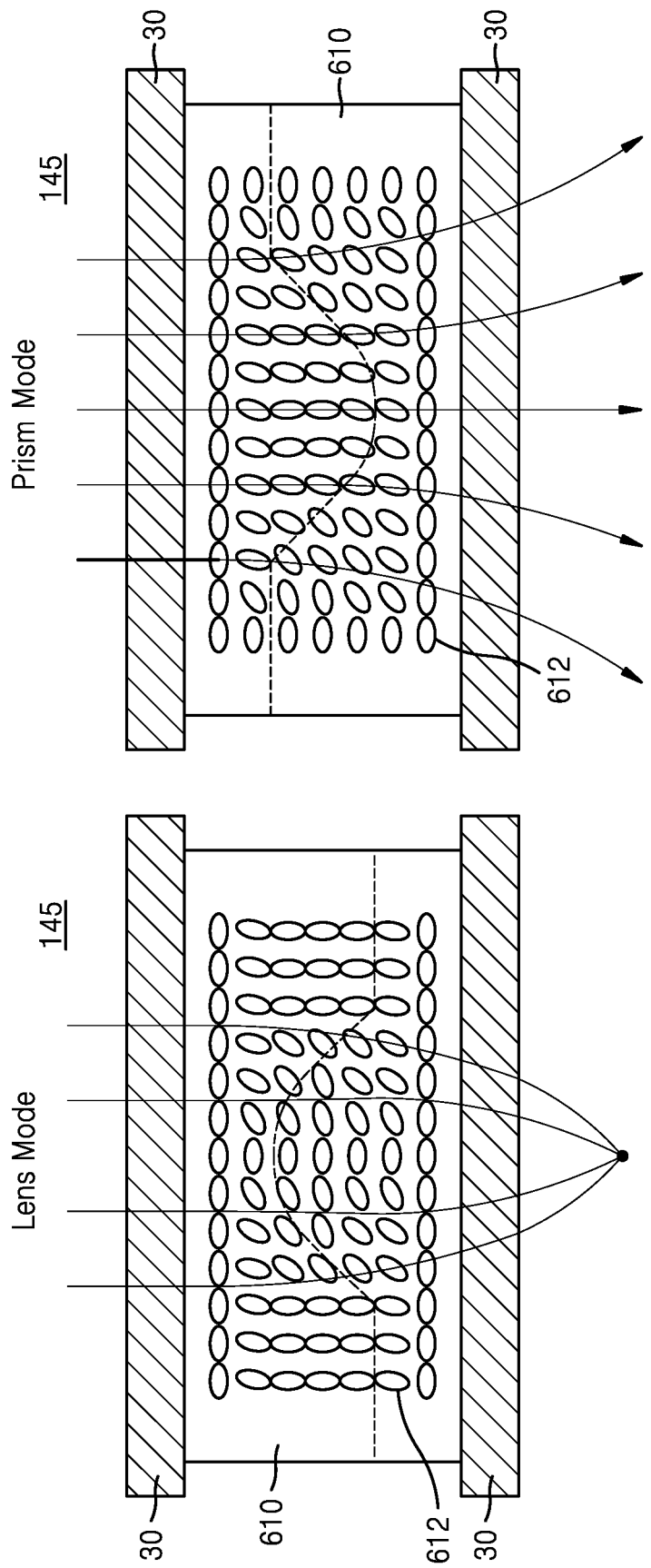
FIG. 5 is a view showing an example in which refractive power of a varifocal lens is changed, according to an embodiment of the disclosure.

FIG. 5 is a view showing an example in which refractive power of the varifocal lens 145 is changed, according to an embodiment of the disclosure.

Referring to FIG. 5, the varifocal lens 145 of FIG. 3A may be implemented, for example, to include an LC layer 610 including LC molecules 612 having a variable orientation angle. In the LC layer 610 of the varifocal lens 145, a control voltage modulated to have a specific phase profile may be applied to an electrode 30 and thus the orientation angle of the LC molecules 612 provided at a specific location in an active area may be changed. When the orientation angle of the LC molecules 612 provided in a specific area of the LC layer 610 is changed, a refractive index of light passing through the LC molecules 612 may be changed. When the refractive index of the light is changed, the refractive power of the varifocal lens 145 may be changed and thus a path of the light passing through the varifocal lens 145 may be changed, thereby changing a vergence. The vergence is an index indicating a degree by which the light passing through the varifocal lens 145 converges or diverges. The vergence may be adjusted according to the refractive power of the varifocal lens 145.

Figure 6:
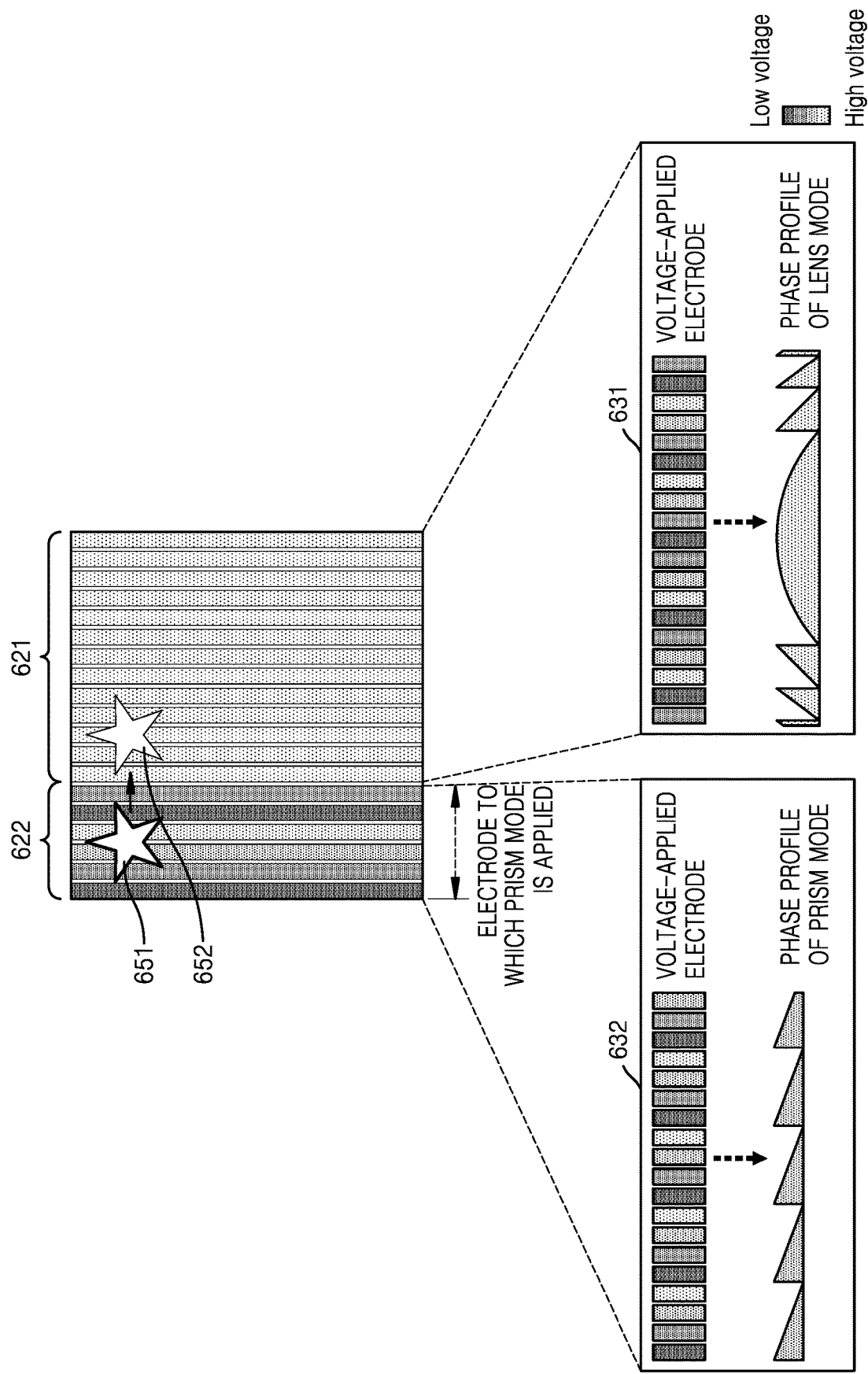
FIG. 6 is a view for describing a prism mode of a varifocal lens, according to an embodiment of the disclosure.

FIG. 6 is a view for describing a prism mode of the varifocal lens 145, according to an embodiment of the disclosure.

The prism mode according to an embodiment of the disclosure is a mode in which refractive power of a specific area of the varifocal lens 145 is changed. The refractive power of the varifocal lens 145 may be changed by changing orientation of LC molecules in the varifocal lens 145.

FIG. 6 shows an example in which a lens mode is applied to a first area 621 of the varifocal lens 145 and a prism mode is applied to a second area 622 of the varifocal lens 145.

According to an embodiment of the disclosure, when the lens mode is applied to the first area 621 of the varifocal lens 145, a voltage may be applied to the first area 621 to have a phase profile 631 corresponding to the lens mode.

According to an embodiment of the disclosure, when the prism mode is applied to the second area 622 of the varifocal lens 145, orientation of the LC molecules may be changed by applying a voltage to the second area 622 to have a phase profile 632 corresponding to the prism mode, and thus the refractive power may be changed. As such, a path of light passing through the second area 622 may be changed.

For example, the prism mode may be applied to the second area 622 of the varifocal lens 145 corresponding to an impaired area of vision of a user. By changing the path of light passing through the second area 622 of the varifocal lens 145 to which the prism mode is applied, a location for displaying an image of a real world object included in the impaired area may be changed from a first location 651 to a second location 652.

According to an embodiment of the disclosure, when a user with visual impairment sees a real scene through the waveguide 142, the user may recognize the real world object, which is included in the impaired area of vision of the user, at another location corresponding to a normal area of vision of the user.

Figure 7:
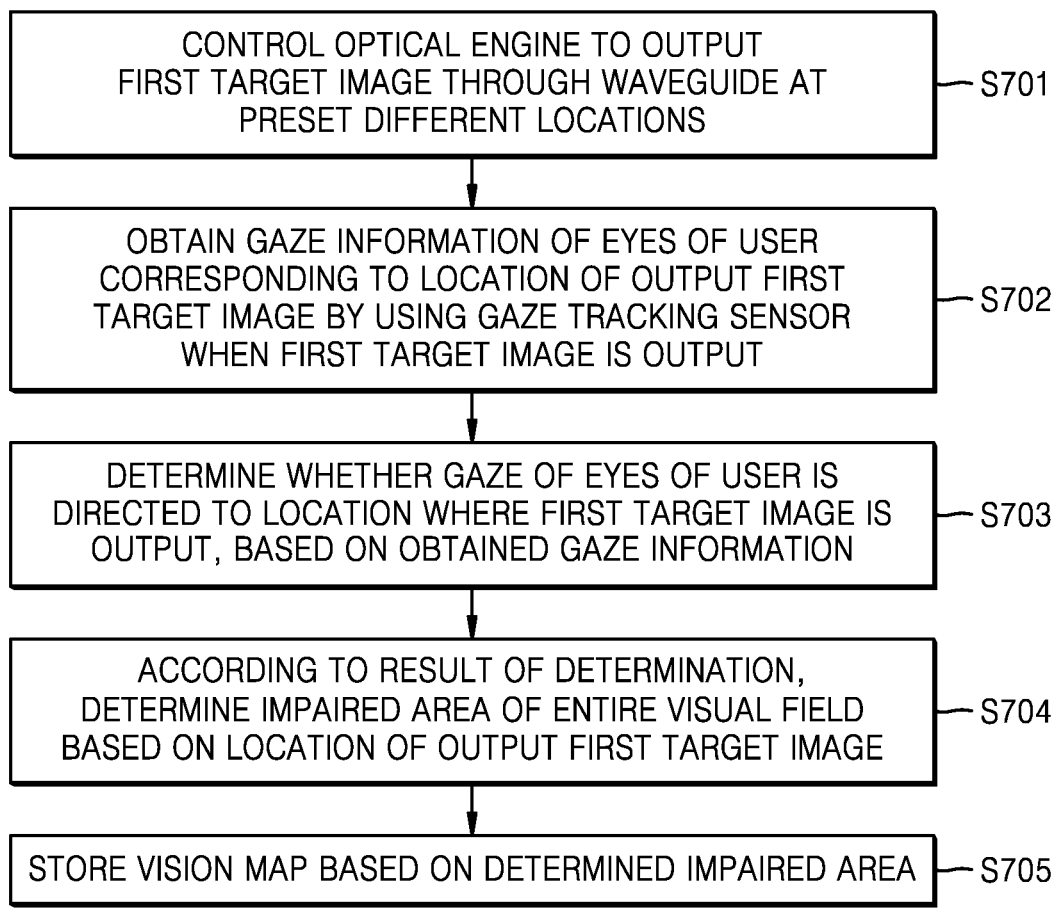
FIG. 7 is a flowchart of a method, performed by an electronic device, of diagnosing visual impairment based on obtaining of gaze information, according to an embodiment of the disclosure.

FIG. 7 is a flowchart of a method, performed by the electronic device 100, of diagnosing visual impairment based on obtaining of gaze information, according to an embodiment of the disclosure.

In operation S701 of FIG. 7, the electronic device 100 may control the optical engine 141 to output a first target image through the waveguide 142 at preset different locations.

According to an embodiment of the disclosure, a diagnosis image for diagnosing visual impairment of a user may include a target image configured as a certain-shaped dot or a certain pattern. For example, the first target image may be a star-shaped, X-shaped, or plus-shaped dot, but is not limited thereto.

According to an embodiment of the disclosure, the preset different locations may include at least one of a plurality of locations spaced apart from each other at certain intervals on the waveguide 142.

The electronic device 100 may control the optical engine 141 to output the first target image through the waveguide 142 sequentially at preset different locations of an entire visual field of the eyes of the user at preset time intervals.

According to an embodiment of the disclosure, the electronic device 100 may output, through the audio outputter 185, guidance information for instructing the user wearing the electronic device 100 to look at the first target image displayed through the waveguide 142 (e.g., 'Look at the displayed dot').

In operation S702 of FIG. 7, the electronic device 100 may obtain gaze information of the eyes of the user corresponding to a location of the output first target image by using the gaze tracking sensor 152 when the first target image is output.

According to an embodiment of the disclosure, the electronic device 100 may obtain the gaze information corresponding to the location of the output first target image by using the gaze tracking sensor 152 at each of timings when the first target image is output sequentially at the preset different locations.

In operation S703 of FIG. 7, the electronic device 100 may determine whether a gaze of the eyes of the user is directed to the location where the first target image is output, based on the obtained gaze information.

The electronic device 100 may determine whether a gaze direction of the eyes of the user converges on the location where the first target image is output at a timing when the first target image is output.

In operation S704 of FIG. 7, according to a result of the determination of operation S703, the electronic device 100 may determine an impaired area of an entire visual field based on the location of the output first target image.

While the first target image (e.g., a star-shaped dot) is being output sequentially at the preset different locations, the electronic device 100 may determine a certain area including the location where the first target image is output when the gaze direction of the eyes of the user does not converge on the location where the first target image is output, as the impaired area.

While the first target image is being output sequentially at the preset different locations, the electronic device 100 may determine a certain area including the location where the first target image is output when the gaze direction of the eyes of the user converges on the location where the first target image is output, as a normal area of vision of the user.

In operation S705 of FIG. 7, the electronic device 100 may store a vision map based on the determined impaired area.

The electronic device 100 may generate the vision map related to the impaired area, and store the vision map in the memory 130. The electronic device 100 may generate the vision map related to the impaired area, and the normal area excluding the impaired area from the entire visual field, and store the vision map in the memory 130.

According to an embodiment of the disclosure, the electronic device 100 may provide assistance to the user to recognize the impaired area of vision of the user, based on the previously stored vision map.

Figure 8:
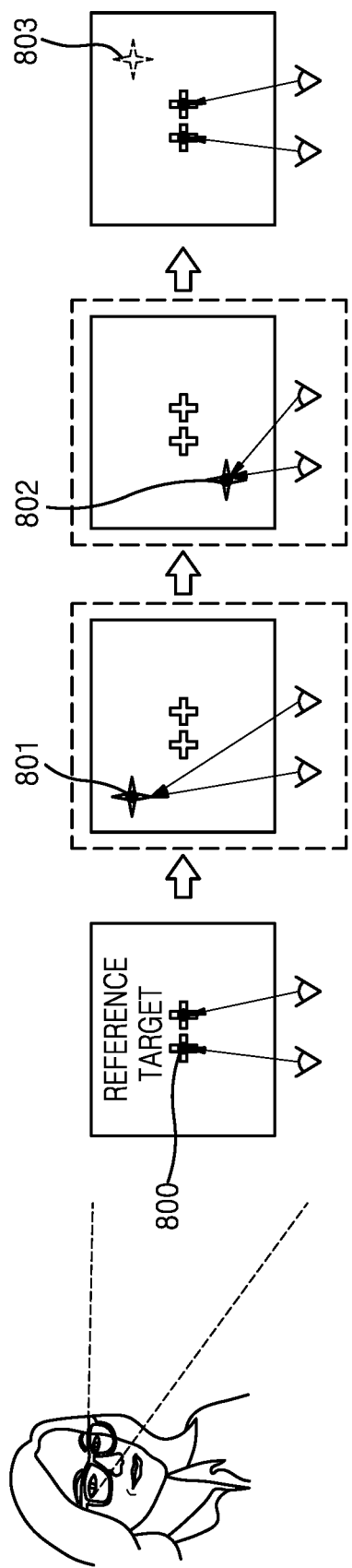
FIG. 8 is a view for describing an example in which an electronic device diagnoses visual impairment based on obtaining of gaze information, according to an embodiment of the disclosure.

FIG. 8 is a view for describing an example in which the electronic device 100 diagnoses visual impairment based on obtaining of gaze information, according to an embodiment of the disclosure.

According to an embodiment of the disclosure, the electronic device 100 may provide a diagnosis image for allowing a user wearing the electronic device 100 to self-diagnose visual impairment of the user. The electronic device 100 may control the optical engine 141 to output a certain diagnosis image through the waveguide 142. The electronic device 100 may induce the user to look at a target image included in the diagnosis image, and determine whether a gaze of the user is directed to a location where the target image is output. The electronic device 100 may determine visual impairment of the user and an impaired area by detecting a location where the target image is displayed but the user may not recognize the target image.

Referring to FIG. 8, at a preliminary stage for diagnosing visual impairment, the electronic device 100 may output a reference target image 800 at a preset location of an entire visual field of the user (e.g., the center of the entire visual field).

For example, upon determining that the gaze of the user converges on the reference target image 800, the electronic device 100 may start diagnosing visual impairment.

The electronic device 100 may provide the diagnosis image including the target image sequentially at different locations.

Referring to FIG. 8, the electronic device 100 may output the target image (e.g., a star-shaped dot) at a first location 801, and obtain gaze information by using the gaze tracking sensor 152. The electronic device 100 may output the target image at a second location 802, and obtain gaze information by using the gaze tracking sensor 152. The electronic device 100 may output the target image at a third location 803, and obtain gaze information by using the gaze tracking sensor 152.

The electronic device 100 may determine whether a gaze of the eyes of the user is directed to a location where the target image is output, based on the gaze information obtained using the gaze tracking sensor 152. For example, the electronic device 100 may determine that the gaze of the eyes of the user is directed to the location where the target image is output when the target image is displayed at the first and second locations 801 and 802, and determine a certain area including the first and second locations 801 and 802 as a normal area of vision of the user.

The electronic device 100 may determine that the gaze of the eyes of the user is not directed to the location where the target image is output when the target image is displayed at the third location 803, and determine a certain area including the third location 803 as an impaired area of vision of the user. The electronic device 100 may determine that the user may not recognize the target image displayed at the third location 803, and determine the certain area including the third location 803 as a lost area of vision of the user.

Figure 9:
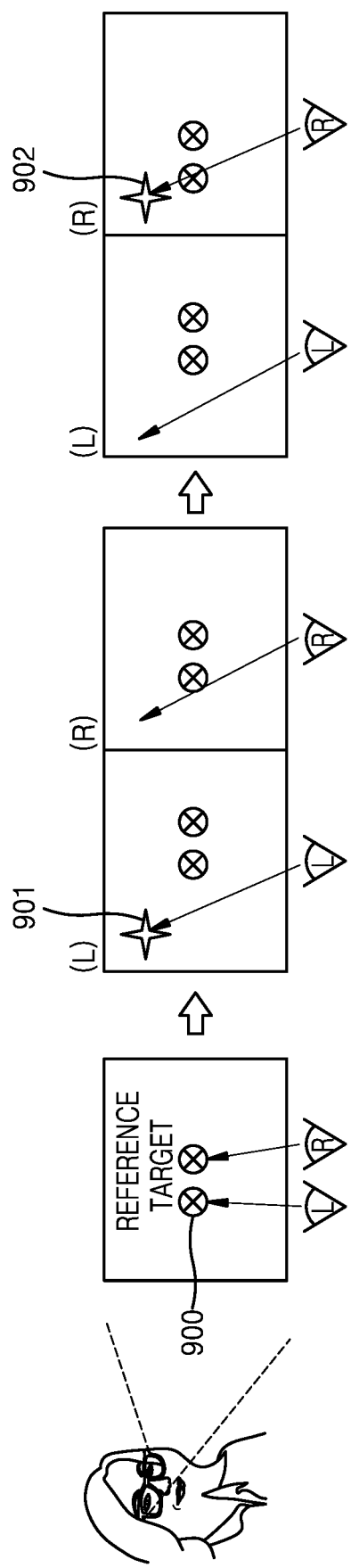
FIG. 9 is a view for describing an example in which an electronic device diagnoses visual impairment of the left or right eye, according to an embodiment of the disclosure.

FIG. 9 is a view for describing an example in which the electronic device 100 diagnoses visual impairment of the left or right eye, according to an embodiment of the disclosure.

Referring to FIG. 9, at a preliminary stage for diagnosing visual impairment, the electronic device 100 may output a reference target image 900 at a preset location of an entire visual field of a user (e.g., the center of the entire visual field). For example, upon determining that a gaze of the user converges on the reference target image 900, the electronic device 100 may start diagnosing visual impairment.

According to an embodiment of the disclosure, in order to detect a lost area of each of the left and right eyes of the user, the electronic device 100 may provide the same diagnosis image including a target image sequentially to the left-eye waveguide 142L (see FIG. 3A) and the right-eye waveguide 142R (see FIG. 3A).

Referring to FIG. 9, the electronic device 100 may output the target image (e.g., a star-shaped dot) at a first location 901 on the left-eye waveguide 142L (see FIG. 3A) (e.g., a top-left side of vision of the user), and then output the target image (e.g., a star-shaped dot) at a second location 902 on the right-eye waveguide 142R (see FIG. 3A) (e.g., a top-left side of vision of the user).

In general, when a user with normal vision opens both eyes, although the target image is output only on the left-eye waveguide 142L (see FIG. 3A), a gaze of the left eye as well as a gaze of the right eye of the user are directed to a location of the target image. Likewise, although the target image is output only on the right-eye waveguide 142R (see FIG. 3A), a gaze of the right eye as well as a gaze of the left eye of the user are directed to a location of the target image.

The electronic device 100 may obtain gaze information by using the gaze tracking sensor 152 when the target image is output at the first location 901 on the left-eye waveguide 142L (see FIG. 3A) (e.g., the top-left side of vision of the user). The electronic device 100 may obtain gaze information by using the gaze tracking sensor 152 when the target image is output at the second location 902 on the right-eye waveguide 142R (see FIG. 3A) (see FIG. 3A) (e.g., the top-left side of vision of the user).

The electronic device 100 may determine whether a gaze of the eyes of the user is directed to a location where the target image is output, based on the gaze information obtained using the gaze tracking sensor 152. For example, the electronic device 100 may determine that the gaze of the eyes of the user is directed to the location where the target image is output when the target image is displayed at the first and second locations 901 and 902 on the left-eye waveguide 142L (see FIG. 3A) and the right-eye waveguide 142R (see FIG. 3A), and determine a certain area including the first and second locations 901 and 902 as a normal area for both of the left and right eyes of the user.

FIG. 10 is a view for describing another example in which the electronic device 100 diagnoses visual impairment of the left or right eye, according to another embodiment of the disclosure.

Referring to FIG. 10, the electronic device 100 may output a target image (e.g., a star-shaped dot) at a third location 903 on the left-eye waveguide 142L (see FIG. 3A) (e.g., a bottom-right side of vision of a user), and then output the target image (e.g., a star-shaped dot) at a fourth location 904 on the right-eye waveguide 142R (see FIG. 3A) (e.g., a bottom-right side of vision of the user).

The electronic device 100 may obtain gaze information by using the gaze tracking sensor 152 when the target image is output at the third location 903 on the left-eye waveguide 142L (see FIG. 3A) (e.g., the bottom-right side of vision of the user). The electronic device 100 may obtain gaze information by using the gaze tracking sensor 152 when the target image is output at the fourth location 904 on the right-eye waveguide 142R (see FIG. 3A) (see FIG. 3A) (e.g., the bottom-right side of vision of the user).

The electronic device 100 may determine whether a gaze of the eyes of the user is directed to a location where the target image is output, based on the gaze information obtained using the gaze tracking sensor 152.

The electronic device 100 may determine that the user may not recognize the target image provided on the left-eye waveguide 142L (see FIG. 3A) or the right-eye waveguide 142R (see FIG. 3A), and determine visual impairment of the left or right eye of the user.

For example, when a user with visual impairment of the right eye opens both eyes, and when the target image is output only on the left-eye waveguide 142L (see FIG. 3A), a gaze of the left eye as well as a gaze of the right eye of the user are directed to a location of the target image. However, when the target image is output only on the right-eye waveguide 142R (see FIG. 3A), the user may not recognize the target image due to visual impairment of the right eye and thus a gaze of the right eye as well as a gaze of the left eye of the user are not directed to a location of the target image.

Referring to FIG. 10, the electronic device 100 may determine that the gaze of the eyes of the user is directed to the location where the target image is output when the target image is output at the third location 903 on the left-eye waveguide 142L (see FIG. 3A), and determine a certain area including the third location 903 as a normal area for the left eye of the user.

Meanwhile, the electronic device 100 may determine that the gaze of the eyes of the user is not directed to the location where the target image is output when the target image is output at the fourth location 904 on the right-eye waveguide 142R (see FIG. 3A), and determine a certain area including the fourth location 904 as a lost area for the right eye of the user.

FIGS. 7 to 10 are merely to describe embodiments of the disclosure, and the scope of the disclosure is not limited thereto.

Figure 11:
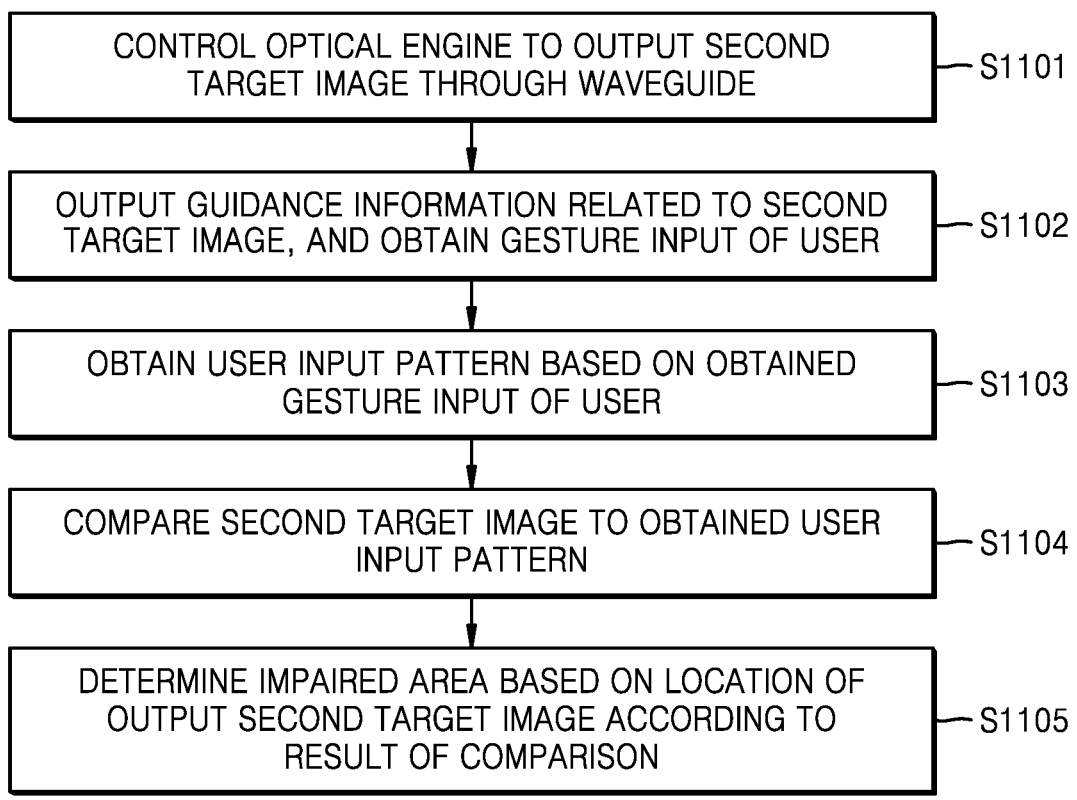
FIG. 11 is a flowchart of a method, performed by an electronic device, of diagnosing visual impairment based on obtaining of a gesture input, according to an embodiment of the disclosure.

FIG. 11 is a flowchart of a method, performed by the electronic device 100, of diagnosing visual impairment based on obtaining of a gesture input, according to an embodiment of the disclosure.

In operation S1101 of FIG. 11, the electronic device 100 may control the optical engine 141 to output a second target image through the waveguide 142.

According to an embodiment of the disclosure, a diagnosis image for diagnosing visual impairment of a user may include a target image configured as a certain-shaped dot or a certain pattern. For example, the second target image may include a plurality of dots aligned at certain intervals, an arbitrary closed curve, or a wave pattern, but is not limited thereto.

In operation S1102 of FIG. 11, the electronic device 100 may output guidance information related to the second target image, and obtain a gesture input of the user by using the depth sensor 153.

According to an embodiment of the disclosure, the electronic device 100 may output, through the audio outputter 185, guidance information for instructing the user wearing the electronic device 100 to trace a pattern of the second target image displayed through the waveguide 142 with a finger (e.g., 'Trace the displayed pattern with your finger').

The electronic device 100 may obtain the gesture input of the user by recognizing a shape or a motion pattern of a hand of the user, based on depth information of fingers sensed by the depth sensor 153.

According to an embodiment of the disclosure, the electronic device 100 may output, through the audio outputter 185, guidance information for instructing the user wearing the electronic device 100 to move the head according to the pattern of the second target image displayed through the waveguide 142 (e.g., 'Move your head according to the displayed pattern').

The electronic device 100 may obtain the gesture input of the user based on a motion pattern of the head of the user sensed using the motion sensor 151.

In operation S1103 of FIG. 11, the electronic device 100 may obtain a user input pattern based on the obtained gesture input of the user. In operation S1104 of FIG. 11, the electronic device 100 may compare the second target image to the obtained user input pattern.

According to an embodiment of the disclosure, the electronic device 100 may determine whether the obtained user input pattern corresponding to the gesture input of the user matches the pattern of the second target image output through the waveguide 142 within a certain range.

In operation S1105 of FIG. 11, the electronic device 100 may determine an impaired area based on a location of the output second target image according to a result of the comparison.

When vision of the eyes of the user includes a distorted area, the certain pattern of the second target image displayed at a location corresponding to the distorted area may appear distorted to the eyes of the user and thus the user input pattern may not match the pattern of the second target image.

When vision of the eyes of the user includes a lost area, the certain pattern of the second target image displayed at a location corresponding to the lost area may not be seen by the eyes of the user and thus the user input pattern may not match the pattern of the second target image.

The electronic device 100 may determine the distorted area or the lost area based on an area where the second target image does not match the user input pattern.

Figure 12:
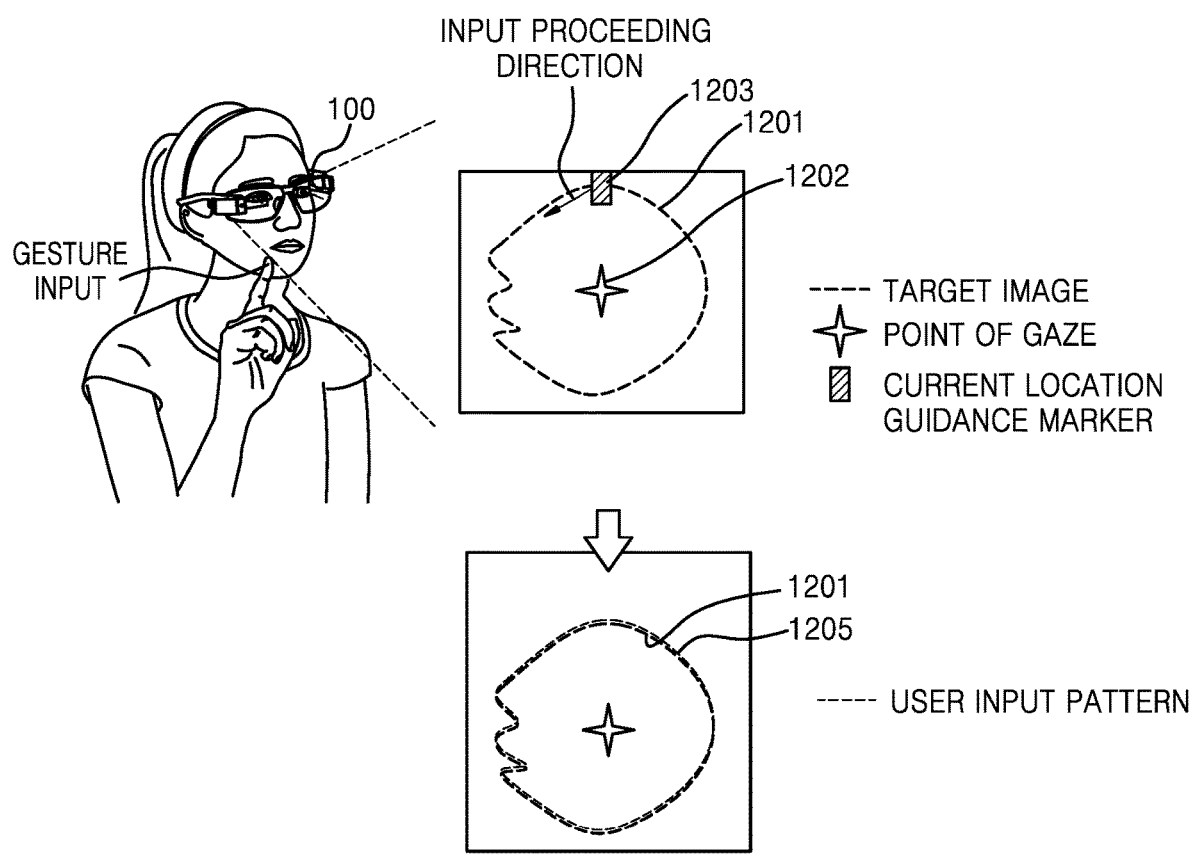
FIG. 12 is a view for describing an example in which an electronic device diagnoses visual impairment based on obtaining of a gesture input, according to an embodiment of the disclosure.

FIG. 12 is a view for describing an example in which the electronic device 100 diagnoses visual impairment based on obtaining of a gesture input, according to an embodiment of the disclosure.

According to an embodiment of the disclosure, the electronic device 100 may provide a diagnosis image for allowing a user wearing the electronic device 100 to self-diagnose visual impairment of the user. The electronic device 100 may control the optical engine 141 to output a certain diagnosis image through the waveguide 142. The electronic device 100 may induce the user to trace a pattern of a target image included in the diagnosis image with a finger while looking at the pattern, and determine whether a user input pattern corresponding to the gesture input of the user matches the pattern of the target image. The electronic device 100 may determine visual impairment of the user and an impaired area by detecting a location where the user may not accurately recognize the pattern of the displayed target image.

Referring to FIG. 12, at a preliminary stage for diagnosing visual impairment, the electronic device 100 may output a point of gaze 1202 at a preset location of an entire visual field of the user (e.g., the center of the entire visual field). The electronic device 100 may induce the user to fix the eyes on the point of gaze 1202 during visual impairment diagnosis based on a gesture input. Upon determining that a gaze of the user converges on the location where the point of gaze 1202 is output, the electronic device 100 may start diagnosing visual impairment.

The electronic device 100 may provide a diagnosis image including a target image 1201 configured as a certain pattern (e.g., an arbitrary dashed closed curve). The electronic device 100 may display a current location guidance marker 1203 at a point of the target image 1201, and induce the user to trace the pattern of the target image 1201 with a finger in an input proceeding direction from a location of the current location guidance marker 1203.

The electronic device 100 may obtain, using the depth sensor 153, a gesture input of the user for tracing the pattern of the target image 1201 with a finger. The electronic device 100 may determine whether a user input pattern 1205 corresponding to the obtained gesture input matches the pattern of the target image 1201.

Referring to FIG. 12, the electronic device 100 may determine that the user input pattern 1205 matches the pattern of the target image 1201 within a certain range, and determine a certain area including a location where the target image 1201 is output, as a normal area of vision of the user.

Figure 13:
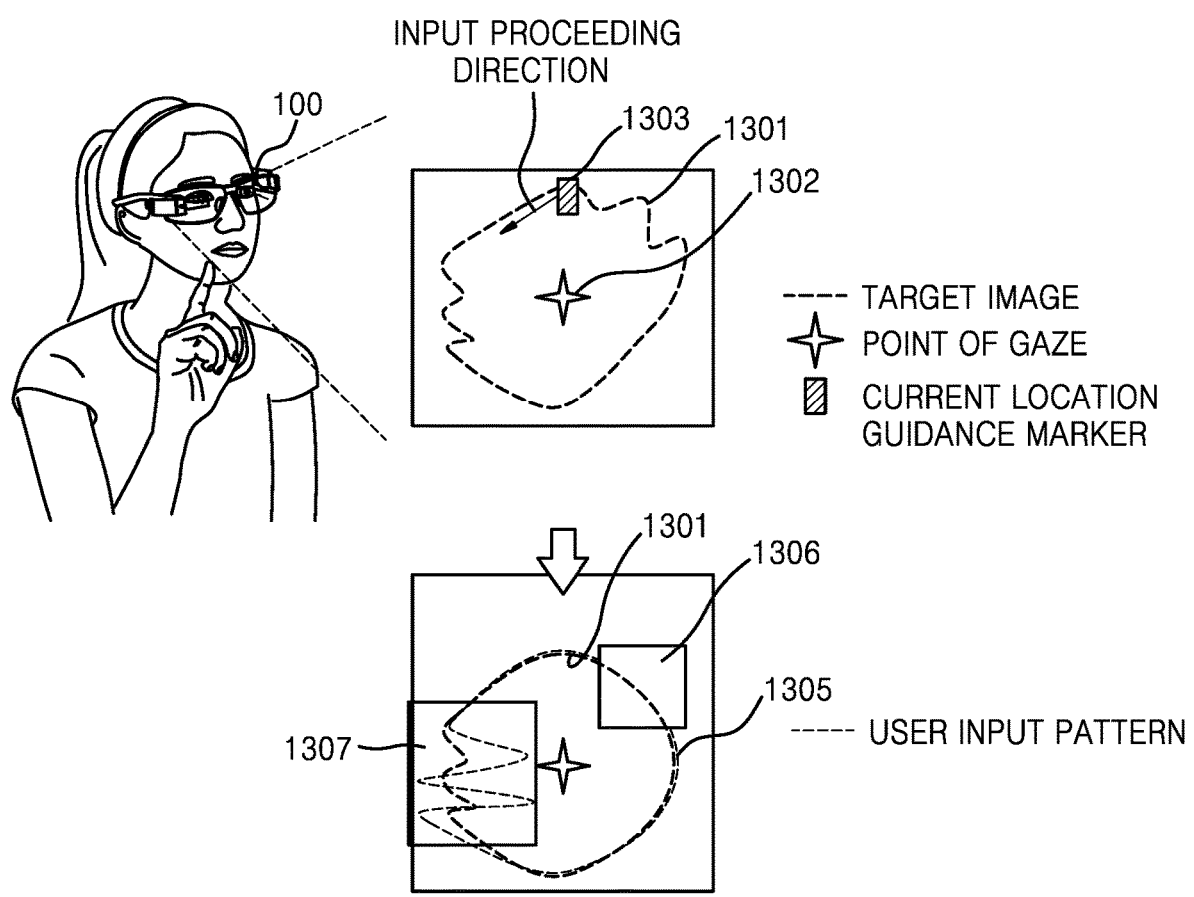
FIG. 13 is a view for describing another example in which an electronic device diagnoses visual impairment based on obtaining of a gesture input, according to an embodiment of the disclosure.

FIG. 13 is a view for describing another example in which the electronic device 100 diagnoses visual impairment based on obtaining of a gesture input, according to an embodiment of the disclosure.

Referring to FIG. 13, the electronic device 100 may output a point of gaze 1302 at a preset location of an entire visual field of a user (e.g., the center of the entire visual field), and induce the user to fix the eyes on the point of gaze 1302 during visual impairment diagnosis based on a gesture input.

The electronic device 100 may provide a diagnosis image including a target image 1301 configured as a certain pattern (e.g., an arbitrary dashed closed curve). The electronic device 100 may induce the user to trace the pattern of the target image 1301 with a finger in an input proceeding direction from a location of a current location guidance marker 1303.

The electronic device 100 may obtain, using the depth sensor 153, a gesture input of the user for tracing the pattern of the target image 1301 with a finger. The electronic device 100 may determine whether a user input pattern 1305 corresponding to the obtained gesture input matches the pattern of the target image 1301.

Referring to FIG. 13, the electronic device 100 may determine that the user input pattern 1305 does not match the pattern of the target image 1301 within a certain range, and determine a certain area including the unmatched area as an impaired area of vision of the user.

The electronic device 100 may determine an area 1307 where the user input pattern 1305 does not match the pattern of the target image 1301 by more than a certain distance, as a distorted area.

The electronic device 100 may determine an area 1306 where the gesture input of the user corresponding to the pattern of the target image 1301 is not obtained, as a lost area.

Figure 14:
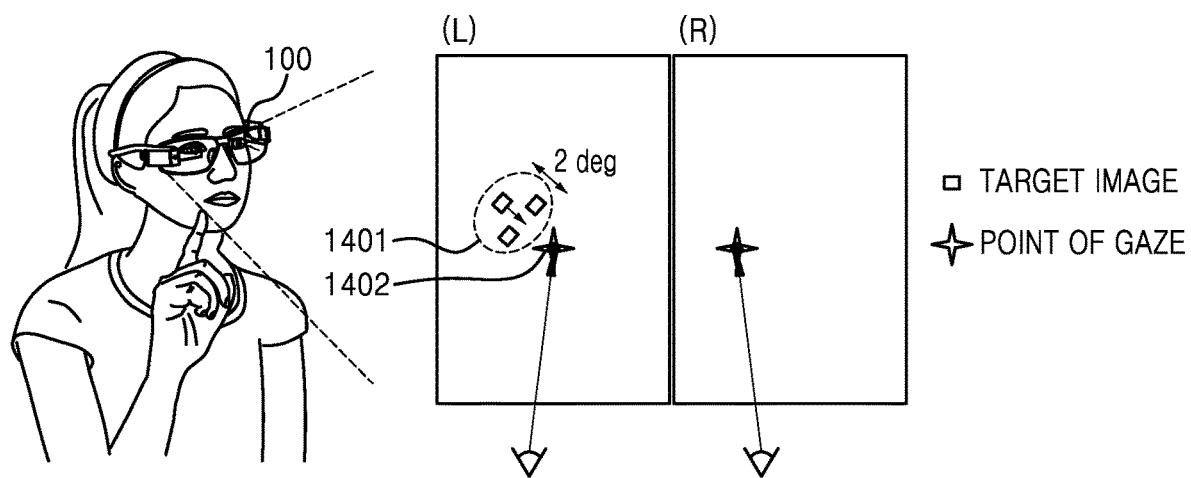
FIG. 14 is a view for describing an example in which an electronic device detects a distorted area, according to an embodiment of the disclosure.

FIG. 14 is a view for describing an example in which the electronic device 100 detects a distorted area, according to an embodiment of the disclosure.

Referring to FIG. 14, the electronic device 100 may output a point of gaze 1402 at a preset location of an entire visual field of a user (e.g., the center of the entire visual field), and induce the user to fix the eyes on the point of gaze 1402 during visual impairment diagnosis based on a gesture input.

The electronic device 100 may provide a diagnosis image including a target image 1401 configured as a certain pattern (e.g., a pattern of alignment of a plurality of dots).

The electronic device 100 may induce the user to trace the pattern of the target image 1401 (e.g., the pattern of alignment of the plurality of dots) with a finger. Alternatively, the electronic device 100 may induce a gesture input for pointing a finger at the plurality of dots one by one according to the pattern of alignment of the plurality of dots.

Referring to FIG. 14, for example, the target image 1401 in which a plurality of dots are aligned in a line and a dot is misaligned by about 2 degrees may be output through the left-eye waveguide 142L (see FIG. 3A).

The electronic device 100 may determine whether a user input pattern corresponding to the gesture input obtained using the depth sensor 153 matches the pattern of the target image 1401.

The electronic device 100 may determine that the user input pattern 1405 matches the pattern of the target image 1401 within a certain range, and determine a certain area including a location where the target image 1401 is displayed, as a normal area of vision of the user.

Alternatively, when a user input for aligning the misaligned dot among the dots included in the target image 1401 with the other adjacent dots in a line is obtained, the electronic device 100 may determine a certain area including the location where the target image 1401 is displayed, as a normal area of vision of the user.

Figure 15:
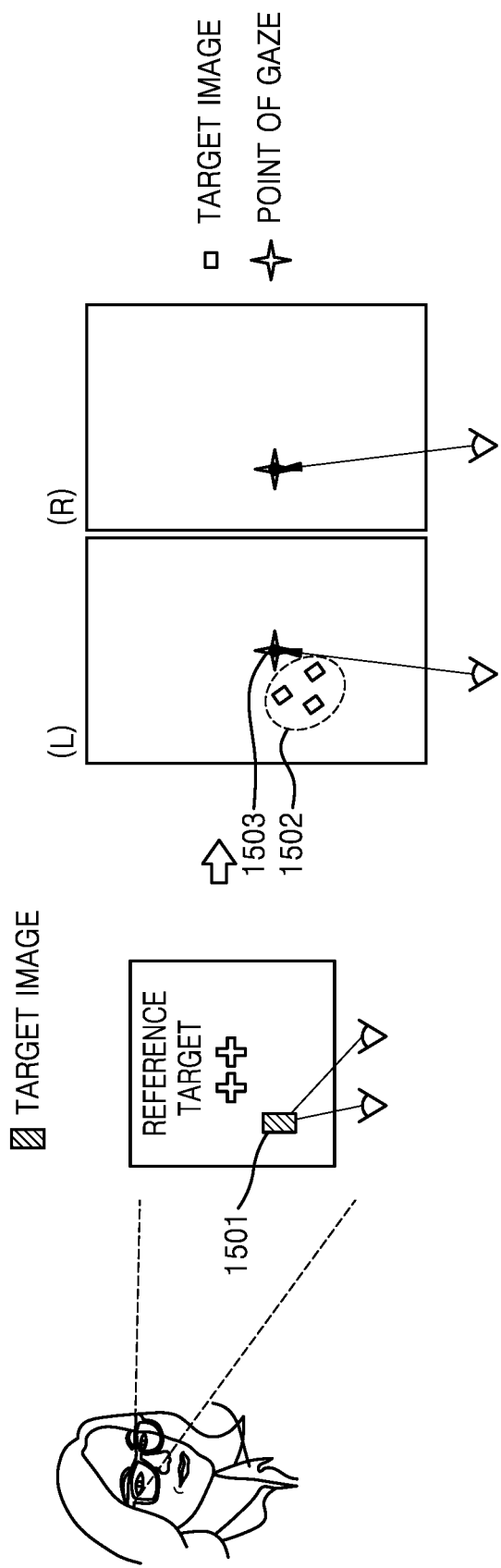
FIG. 15 is a view for describing another example in which an electronic device detects a distorted area, according to an embodiment of the disclosure.

FIG. 15 is a view for describing another example in which the electronic device 100 detects a distorted area, according to an embodiment of the disclosure.

According to an embodiment of the disclosure, the electronic device 100 may determine whether an area, which is determined not to be a lost area of vision of a user based on obtaining of gaze information, is a distorted area.

According to an embodiment of the disclosure, the distorted area refers to an area which is visible but appears distorted to the eyes of the user. Therefore, although the user may recognize one dot when the dot is displayed on the distorted area of vision of the user, the use may not accurately recognize a pattern of alignment of a plurality of dots aligned and displayed on the distorted area.

According to an embodiment of the disclosure, in order to diagnose a lost area of vision of the user based on obtaining of gaze information, the electronic device 100 may induce the user to look at a target image included in a diagnosis image, and determine whether a gaze of the user is directed to a location where the target image is output.

Referring to FIG. 15, the electronic device 100 may output a first target image 1501 (e.g., a rectangular dot) at a bottom-left side of vision of the user, and obtain gaze information by using the gaze tracking sensor 152.

The electronic device 100 may determine whether a gaze of the eyes of the user is directed to the location where the first target image 1501 is output, based on the gaze information obtained using the gaze tracking sensor 152. For example, upon determining that the gaze of the eyes of the user is directed to the location where the first target image 1501 is output when the first target image 1501 is displayed at the bottom-left side of vision of the user, the electronic device 100 may determine that a certain area including the bottom-left side of vision of the user is not a lost area.

Referring to FIG. 15, in order to diagnose a distorted area of vision of the user based on obtaining of a gesture input, the electronic device 100 may output a second target image 1502 configured as a pattern of alignment of a plurality of dots, at the same location where the first target image 1501 is output.

The electronic device 100 may output a point of gaze 1503 at a preset location of an entire visual field of the user (e.g., the center of the entire visual field), and induce the user to fix the eyes on the point of gaze 1503 during visual impairment diagnosis based on a gesture input.

The electronic device 100 may induce the user to trace the pattern of the second target image 1502 with a finger. Alternatively, the electronic device 100 may induce a gesture input for pointing a finger at the plurality of dots one by one according to the pattern of alignment of the plurality of dots.

The electronic device 100 may determine that a user input pattern corresponding to the gesture input obtained using the depth sensor 153 does not match the pattern of the second target image 1502 within a certain range, and determine a certain area including the location where the second target image 1502 is displayed, as a distorted area of vision of the user.

The electronic device 100 may determine that the user may not accurately recognize the pattern of alignment of the second target image 1502 output through the left-eye waveguide 142L (see FIG. 3A), and determine a certain area including the location where the second target image 1502 is displayed on an entire visual field of the left eye of the user, as a distorted area.

Figure 16:
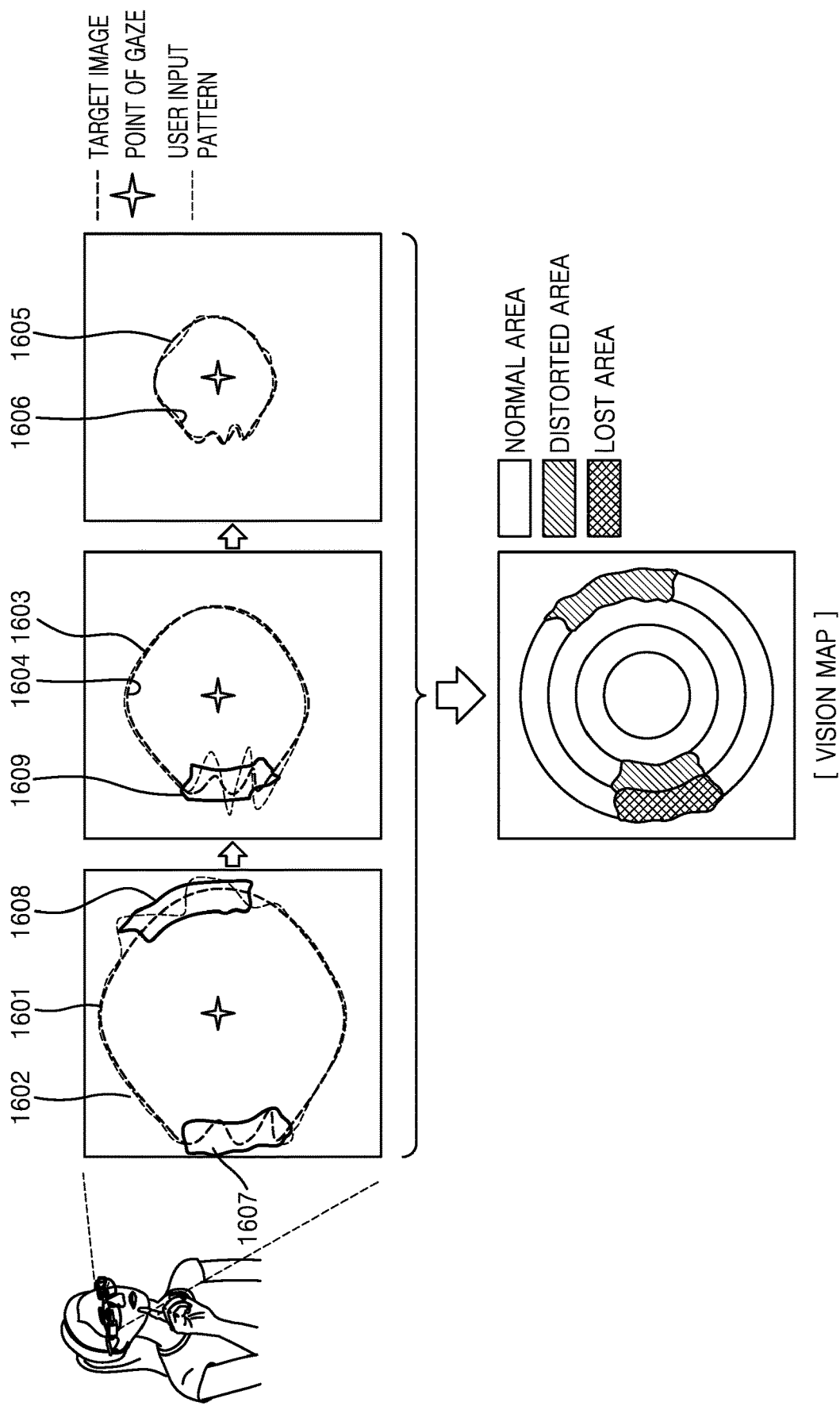
FIG. 16 is a view for describing another example in which an electronic device detects an impaired area of vision of a user, according to an embodiment of the disclosure.

FIG. 16 is a view for describing another example in which the electronic device 100 detects an impaired area of vision of a user, according to an embodiment of the disclosure.

According to an embodiment of the disclosure, the electronic device 100 may provide a diagnosis image by gradually reducing a radius of a target image configured as a circular closed curve.

The electronic device 100 may provide a diagnosis image by gradually reducing the size of an arbitrary circular closed curve including a wave pattern from the periphery to the center of vision of a user, and thus perform more precise diagnosis by minimizing a non-diagnosed area in an entire visual field of the user.

According to an embodiment of the disclosure, the electronic device 100 may induce the user wearing the electronic device 100 to trace the pattern of the target image with a finger. The electronic device 100 may obtain a gesture input of the user for tracing the pattern of the target image with a finger, by using the depth sensor 153.

Referring to FIG. 16, the electronic device 100 may determine whether a first user input pattern 1602 corresponding to an obtained gesture input matches a pattern of a first target image 1601. The electronic device 100 may determine whether a second user input pattern 1604 corresponding to an obtained gesture input matches a pattern of a second target image 1603. The electronic device 100 may determine whether a third user input pattern 1606 corresponding to an obtained gesture input matches a pattern of a third target image 1605.

According to an embodiment of the disclosure, the electronic device 100 may determine an area 1607 where the gesture input of the user corresponding to the pattern of the first target image 1601 is not obtained, as a lost area.

The electronic device 100 may determine an area 1608 where the first user input pattern 1602 does not match the pattern of the first target image 1601 by more than a certain distance, as a distorted area. The electronic device 100 may determine an area 1609 where the second user input pattern 1604 does not match the pattern of the second target image 1603 by more than a certain distance, as a distorted area.

The electronic device 100 may determine an area excluding the distorted and lost areas from the entire visual field, as a normal area of vision of the user.

The electronic device 100 may determine that the third user input pattern 1606 matches the pattern of the third target image 1605 within a certain range, and determine a certain area including a location where the third target image 1605 is output, as a normal area of vision of the user.

According to an embodiment of the disclosure, the electronic device 100 may generate a vision map related to the normal area of vision of the user, and an impaired area including the distorted and lost areas, and store the vision map in the memory 130.

According to an embodiment of the disclosure, the electronic device 100 may provide assistance to the user to recognize the impaired area of vision of the user, based on the vision map.

FIGS. 11 to 16 are merely to describe embodiments of the disclosure, and the scope of the disclosure is not limited thereto.

Figure 17:
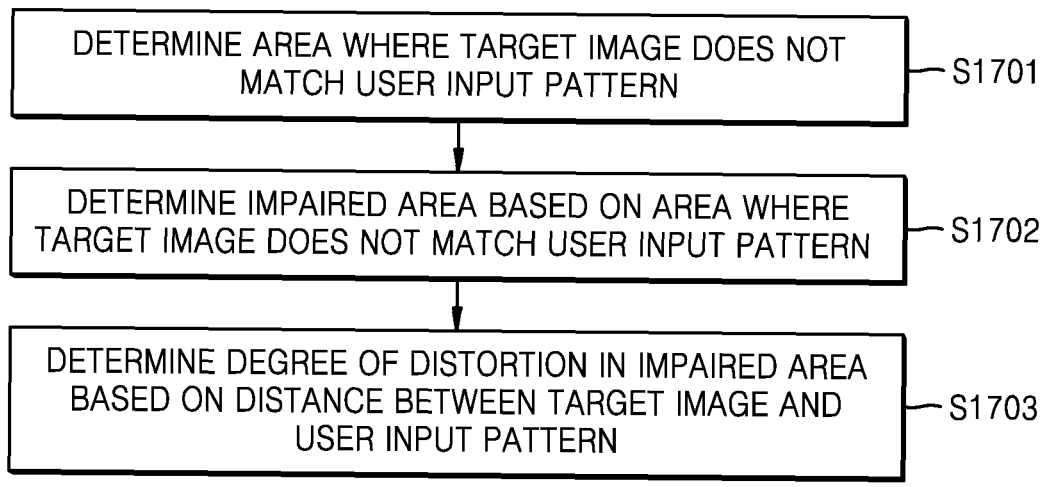
FIG. 17 is a flowchart of a method, performed by an electronic device, of calculating a degree of distortion, according to an embodiment of the disclosure.

FIG. 17 is a flowchart of a method, performed by the electronic device 100, of calculating a degree of distortion, according to an embodiment of the disclosure.

According to an embodiment of the disclosure, when vision of a user with visual impairment includes a distorted area, a degree of distortion may vary. The electronic device 100 may diagnose the degree of distortion through visual impairment diagnosis based on obtaining of a gesture input.

In operation S1701 of FIG. 17, the electronic device 100 may determine an area where a target image does not match a user input pattern. In operation S1702 of FIG. 17, the electronic device 100 may determine an impaired area based on the area where the target image does not match the user input pattern.

According to an embodiment of the disclosure, the electronic device 100 may induce the user to trace a pattern of the target image included in a diagnosis image with a finger while looking at the pattern, and determine whether the user input pattern corresponding to the gesture input of the user matches the pattern of the target image. The electronic device 100 may determine the impaired area of vision of the user by detecting a location where the user may not accurately recognize the pattern of the displayed target image.

In operation S1703 of FIG. 17, the electronic device 100 may determine a degree of distortion in the impaired area based on a distance between the target image and the user input pattern.

According to an embodiment of the disclosure, the electronic device 100 may calculate the distance between the target image and the user input pattern in the area where the target image does not match the user input pattern. The electronic device 100 may determine the degree of distortion in a distorted area based on the calculated distance. The electronic device 100 may determine a higher degree of distortion for a longer distance.

Figure 18:
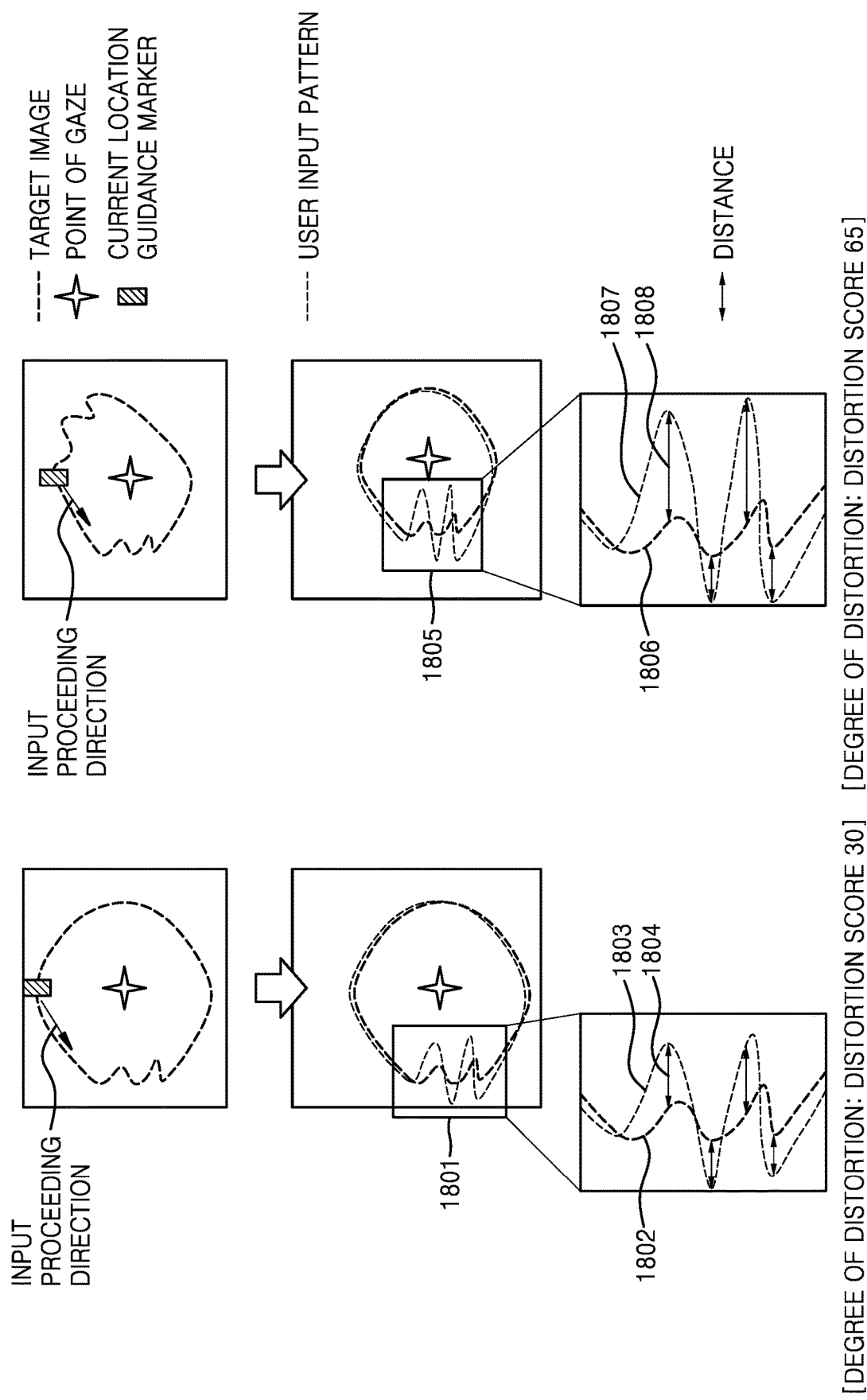
FIG. 18 is a view for describing an example in which an electronic device calculates a degree of distortion, according to an embodiment of the disclosure.

FIG. 18 is a view for describing an example in which the electronic device 100 calculates a degree of distortion, according to an embodiment of the disclosure.

According to an embodiment of the disclosure, the electronic device 100 may determine a degree of distortion in a distorted area of vision of a user by calculating a distance between a target image and a user input pattern corresponding to a gesture input of the user.

Referring to FIG. 18, for example, the electronic device 100 may calculate a first distance 1804 between a first user input pattern 1803 and a first target image 1802 in a first distorted area 1801. For example, the electronic device 100 may calculate a second distance 1808 between a second user input pattern 1807 and a second target image 1806 in a second distorted area 1805.

According to an embodiment of the disclosure, the electronic device 100 may determine a higher degree of distortion for a longer distance, and determine a lower degree of distortion for a shorter distance.

According to an embodiment of the disclosure, the electronic device 100 may quantify the degree of distortion to, for example, score 30 or score 65, according to a predetermined criterion.

FIGS. 17 and 18 are merely to describe embodiments of the disclosure, and the scope of the disclosure is not limited thereto.

Figure 19:
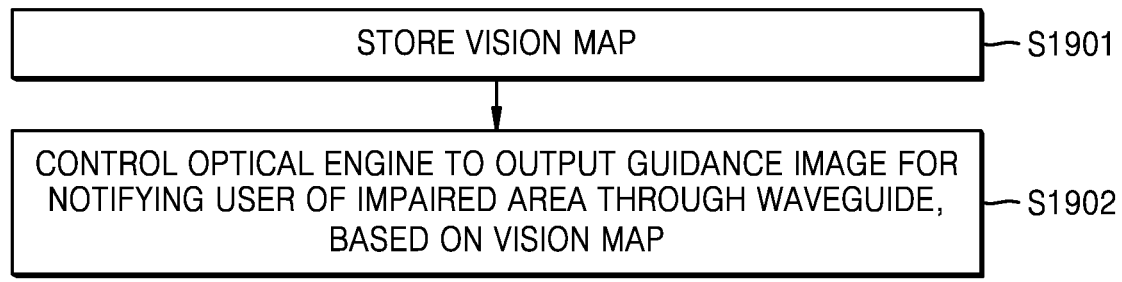
FIG. 19 is a flowchart of a method, performed by an electronic device, of outputting a guidance image for notifying an impaired area of vision of a user, according to an embodiment of the disclosure.

FIG. 19 is a flowchart of a method, performed by the electronic device 100, of outputting a guidance image for notifying an impaired area of vision of a user, according to an embodiment of the disclosure.

In operation S1901 of FIG. 19, the electronic device 100 may store a vision map.

According to an embodiment of the disclosure, the electronic device 100 may generate the vision map including information about an impaired area, by diagnosing visual impairment of a user wearing the electronic device 100, and store the vision map in the memory 130.

In operation S1902 of FIG. 19, the electronic device 100 may control the optical engine 141 to output a guidance image for notifying the user of the impaired area through the waveguide 142, based on the vision map.

According to an embodiment of the disclosure, the guidance image may include, for example, a solid or dashed outline indicating the boundary of the impaired area, but is not limited thereto.

Figure 20:
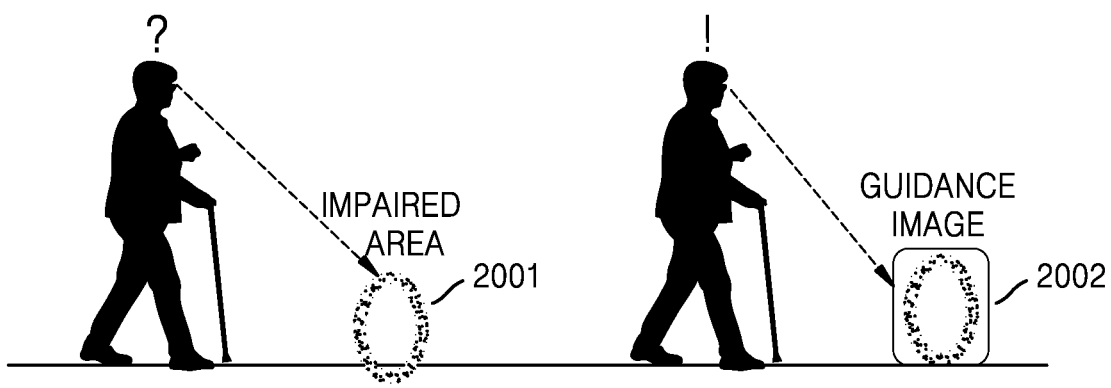
FIG. 20 is a view for describing an example in which an electronic device outputs a guidance image for notifying an impaired area, according to an embodiment of the disclosure.

FIG. 20 is a view for describing an example in which the electronic device 100 outputs a guidance image for notifying an impaired area, according to an embodiment of the disclosure.

Referring to FIG. 20, the electronic device 100 may output a guidance image 2002 indicating a location of an impaired area 2001 of vision of a user wearing the electronic device 100, in the form of an outline of the impaired area 2001 on a normal area outside the impaired area 2001 in a real scene seen by the user through the waveguide 142.

According to an embodiment of the disclosure, when the user wearing the electronic device 100 sees the real scene, the user may recognize that the real scene seen by the user includes the impaired area of vision of the user, based on the guidance image.

Figure 21:
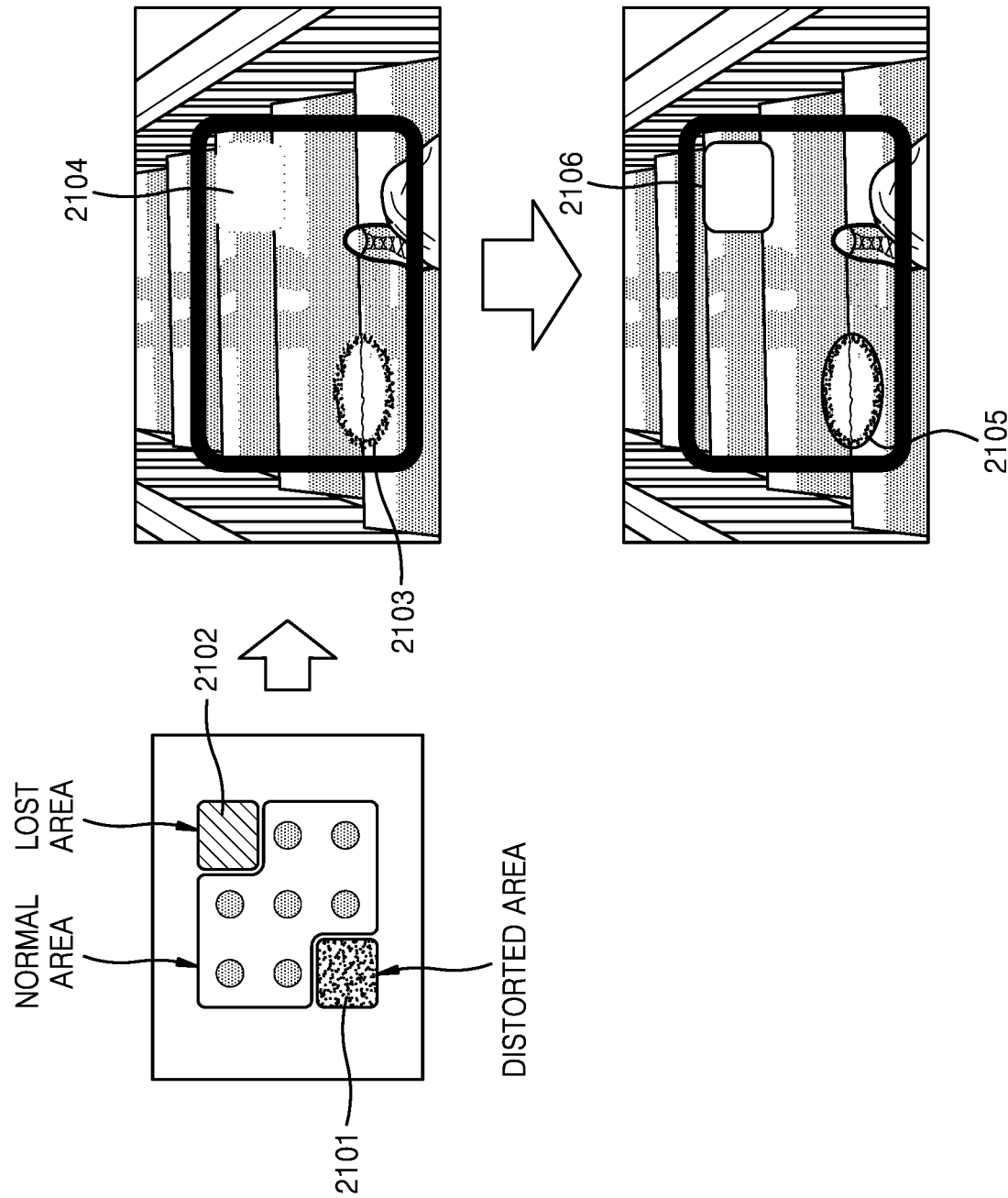
FIG. 21 is a view for describing an example in which an electronic device outputs a guidance image on a display, according to an embodiment of the disclosure.

FIG. 21 is a view for describing an example in which the electronic device 100 outputs a guidance image on a display, according to an embodiment of the disclosure. The scene of FIG. 21 is that of a person descending a staircase.

Referring to FIG. 21, the electronic device 100 may identify a distorted area 2101 and a lost area 2102 in an entire visual field of a user wearing the electronic device 100, based on a previously stored vision map.

According to an embodiment of the disclosure, the entire visual field of the eyes of the user may include an entire display area on the waveguide 142 of the electronic device 100.

The electronic device 100 may determine a location of a distorted area 2103 on the waveguide 142 corresponding to the distorted area 2101, and determine a location of a lost area 2104 on the waveguide 142 corresponding to the lost area 2102, on the entire display area of the waveguide 142.

The electronic device 100 may control the optical engine 141 to display a first guidance image 2105 indicating an outline of the distorted area 2103 and a second guidance image 2106 indicating an outline of the lost area 2104, through the waveguide 142.

According to an embodiment of the disclosure, when the user sees a real scene through the waveguide 142, the user may recognize that a real world object of the real scene, which is located in a direction and at a distance where a guidance image is displayed, is not accurately visible due to visual impairment of the user. In FIG. 21, at the place and time illustrated a portion of a step of the staircase is a real world object in the field of view of the outline (second guidance image 2106) of the lost area 2104.

FIGS. 19 to 21 are merely to describe embodiments of the disclosure, and the scope of the disclosure is not limited thereto.

Figure 22:
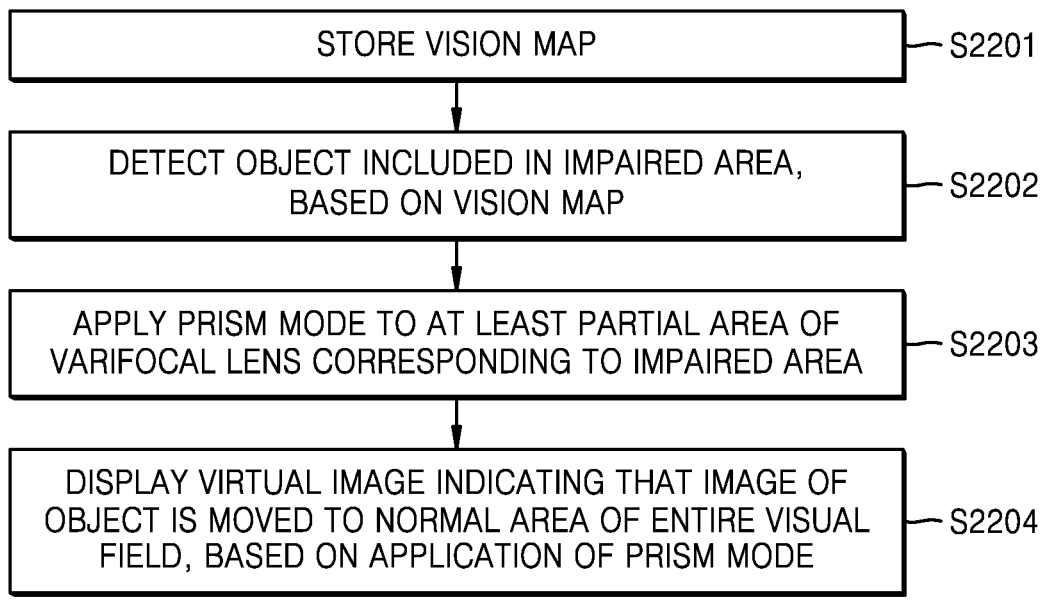
FIG. 22 is a flowchart of a method, performed by an electronic device, of outputting an object based on a prism mode, according to an embodiment of the disclosure.

FIG. 22 is a flowchart of a method, performed by the electronic device 100, of outputting an object based on a prism mode, according to an embodiment of the disclosure.

In operation S2201 of FIG. 22, the electronic device 100 may store a vision map.

According to an embodiment of the disclosure, the electronic device 100 may generate the vision map including information about an impaired area, by diagnosing visual impairment of a user wearing the electronic device 100, and store the vision map in the memory 130.

In operation S2202 of FIG. 22, the electronic device 100 may detect an object included in the impaired area, based on the vision map.

According to an embodiment of the disclosure, the electronic device 100 may identify the impaired area including distorted and lost areas in an entire visual field of the user wearing the electronic device 100, based on the previously stored vision map.

According to an embodiment of the disclosure, the electronic device 100 may determine whether a real world object is present in the impaired area of vision of the user.

The electronic device 100 may obtain information indicating whether the real world object is present in front of the electronic device 100, a direction and distance of the real world object, etc., based on depth information of the real world object sensed by the depth sensor 153.

In operation S2203 of FIG. 22, the electronic device 100 may apply a prism mode to at least a partial area of the varifocal lens 145 corresponding to the impaired area. The electronic device 100 may apply the prism mode to at least the partial area of the varifocal lens 145 in such a manner that an image of the object detected in operation S2202 is refracted and moved to a normal area of vision of the user.

The prism mode according to an embodiment of the disclosure is a mode in which refractive power of a specific area of the varifocal lens 145 is changed. The refractive power of the varifocal lens 145 may be changed by changing orientation of LC molecules in the varifocal lens 145.

The electronic device 100 may exert control to change a path of light passing through the specific area of the varifocal lens 145 corresponding to the impaired area, by applying the prism mode to the specific area of the varifocal lens 145 corresponding to the impaired area of vision of the user.

When the prism mode is applied to the specific area of the varifocal lens 145 corresponding to the impaired area, a voltage may be applied to have a phase profile corresponding to the prism mode, and thus the refractive power may be changed. As such, the path of light passing through the specific area of the varifocal lens 145 corresponding to the impaired area may be changed, and thus the image of the object included in the impaired area may be refracted and output on the normal area of the entire visual field.

In operation S2204 of FIG. 22, the electronic device 100 may control the optical engine 141 to display a virtual image indicating that the image of the object is moved to the normal area of the entire visual field, based on application of the prism mode.

When the image of the object detected in the impaired area is refracted by the varifocal lens 145 to which the prism mode is applied, and is moved to the normal area, the electronic device 100 may control the optical engine 141 to output a virtual image, e.g., a mark, an icon, or a certain image, for notifying the user that the image is moved to the normal area so as to be visible to the user.

Figure 23:
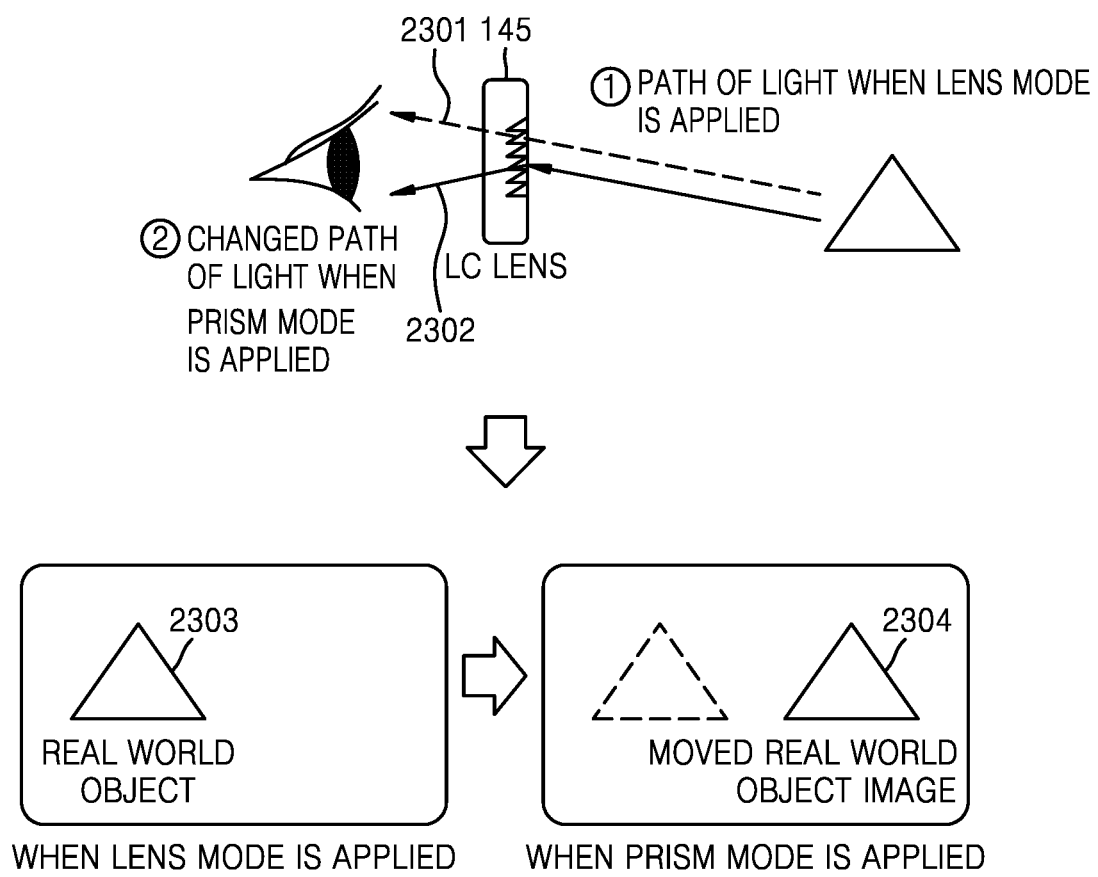
FIG. 23 is a view for describing application of a prism mode, according to an embodiment of the disclosure.

FIG. 23 is a view for describing application of a prism mode, according to an embodiment of the disclosure.

According to an embodiment of the disclosure, a prism mode may be applied to at least a partial area of the varifocal lens 145 corresponding to an impaired area of vision of a user.

When the prism mode is applied to a specific area of the varifocal lens 145 corresponding to the impaired area of vision of the user, a path of light passing through the specific area may be changed and thus an image of an object included in the impaired area may be refracted and moved to a normal area of vision of the user.

For example, compared to a path 2301 of light passing through the varifocal lens 145 when a lens mode is applied, when the prism mode is applied to the specific area of the varifocal lens 145, light passing through the specific area may be refracted to a path 2302 of light. When the prism mode is applied, orientation of LC molecules may be changed by applying a voltage to the specific area of the varifocal lens 145 to have the phase profile 632 (see FIG. 6) corresponding to the prism mode, and thus refractive power may be changed.

As such, an image of a real world object displayed at a first location 2303 in the specific area of the varifocal lens 145 when the lens mode is applied may be moved to a second location 2304 in the normal area of vision of the user due to a change of a path of light passing through the specific area when the prism mode is applied.

Figure 24:
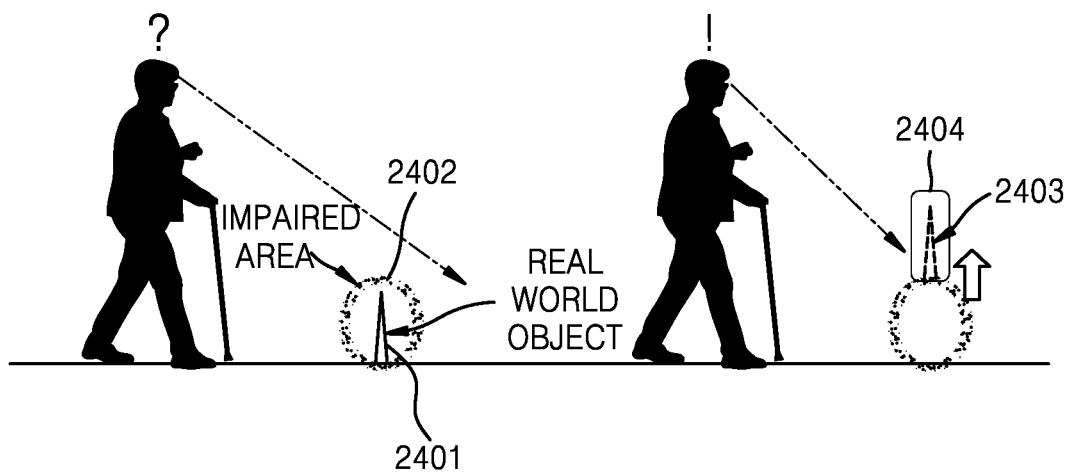
FIG. 24 is a view for describing an example in which an electronic device outputs an object based on a prism mode, according to an embodiment of the disclosure.

FIG. 24 is a view for describing an example in which the electronic device 100 outputs an object based on a prism mode, according to an embodiment of the disclosure.

Referring to FIG. 24, when a user wearing the electronic device 100 sees a real scene, the user may not recognize a real world object 2401 included in an impaired area 2402 of vision of the user.

According to an embodiment of the disclosure, the electronic device 100 may exert control to move an image of the real world object 2401 included in the impaired area 2402 to a partial area in a normal area of vision of the user, by applying a prism mode to a specific area of the varifocal lens 145 corresponding to the impaired area 2402 of vision of the user.

As such, when the user wearing the electronic device 100 sees the real scene, the user may recognize the real world object 2401, which is included in the impaired area 2402 of vision of the user and thus is not visible to the user, at another location as a moved real world object image 2403.

According to an embodiment of the disclosure, the electronic device 100 may output a virtual certain icon or image 2404 around the moved real world object image 2403 in such a manner that the user may recognize that the real world object image 2403 visible to the user in the normal area of vision of the user is moved from the impaired area of vision of the user.

FIGS. 22 to 24 are merely to describe embodiments of the disclosure, and the scope of the disclosure is not limited thereto.

Meanwhile, the afore-described embodiments of the disclosure may be written as computer-executable programs, and be implemented by a general-purpose digital computer for operating the programs by using a computer-readable medium. Data structures used in the afore-described embodiments of the disclosure may be recorded on the computer-readable medium via various means. The afore-described embodiments of the disclosure may be implemented in the form of a recording medium including computer-executable instructions, e.g., computer-executable program modules. For example, methods implemented as software modules or algorithms may be stored in a computer-readable recording medium as computer-readable and—executable codes or program commands.

The computer-readable medium may be an arbitrary recording medium accessible by a computer, and include volatile, non-volatile, detachable, and non-detachable media. Examples of the computer-readable medium include magnetic storage media (e.g., read-only memory (ROM), floppy disks, and hard disks) and optical recording media (e.g., compact disc-ROM (CD-ROM) and digital versatile discs (DVDs)), but are not limited thereto. The computer-readable medium may include a computer storage medium and a communication medium.

A plurality of computer-readable recording media may be distributed over network-coupled computer systems, and data, e.g., program instructions and codes, stored in the distributed recording media may be executed by at least one computer.

Particular implementations described herein merely correspond to embodiments of the disclosure and do not limit the scope of the disclosure in any way. For brevity, descriptions of known electronic configurations, control systems, software, and other functional aspects of the systems may not be provided herein.

While the disclosure has been particularly shown and described with reference to embodiments of the disclosure, it will be understood by one of ordinary skill in the art that various changes in form and details may be made therein without departing from the scope of the disclosure. Therefore, it should be understood that the afore-described embodiments of the disclosure are illustrative in all aspects and do not limit the disclosure. For example, each element described as a single element may be implemented in a distributed manner and, likewise, elements described as distributed elements may be implemented in a combined manner.

All examples and illustrative terms, e.g., "etc.", used herein are merely to describe the disclosure in detail and the scope of the disclosure is not limited by those examples and illustrative terms unless defined in the claims.

Moreover, no element is essential for implementation of the disclosure unless the element is particularly described as being "essential" or "critical".

It will be understood by one of ordinary skill in the art that the embodiments of the disclosure may be modified without departing from the scope of the disclosure.

It should be understood that various changes in form and details may be made in the embodiments of the disclosure and that the embodiments of the disclosure cover all modifications, equivalents, and alternatives falling within the scope of the disclosure. Therefore, the afore-described embodiments of the disclosure should be considered in a descriptive sense only and not for purposes of limitation.

The scope of the disclosure is defined not by the detailed description of the disclosure but by the appended claims, and all variations derived from the scope defined by the claims and their equivalents will be construed as being included in the scope of the disclosure.

As used herein, the term " . . . unit" or "module" denotes an entity for performing at least one function or operation, and may be implemented as hardware, software, or a combination of hardware and software.

The "unit" or "module" may also be implemented by a program stored in an addressable storage medium and executable by a processor.

For example, the term "unit" or "module" may be implemented by elements (e.g., software elements, object-oriented software elements, class elements, and task elements), processes, functions, attributes, procedures, subroutines, segments of program code, drivers, firmware, micro-codes, circuits, data, a database, data structures, tables, arrays, or variables.

As used herein, the expression "A may include one of a1, a2, and a3" broadly means that an example of an element that may be included in element A is a1, a2, or a3.

The expression does not limit the element that may be included in element A, to a1, a2, or a3. Therefore, it should be noted that the expression is not restrictively construed to exclude elements other than a1, a2, and a3, from examples of the element that may be included in A.

The expression means that A may include a1, include a2, or include a3. The expression does not mean that elements included in A are always selectively determined within a certain set. For example, it should be noted that the expression is not restrictively construed to limit the element included in element A, to a1, a2, or a3 selected from a set including a1, a2, and a3.

The invention claimed is:

1. An electronic device comprising:
a display comprising an optical engine and a waveguide;
a gaze tracking sensor;
a memory configured to store one or more instructions; and
a processor configured to execute the one or more instructions to:
control the optical engine to output a first target image through the waveguide at preset different locations;
obtain gaze information of eyes of a user corresponding to a location of the first target image by using the gaze tracking sensor;
determine whether a gaze of the eyes of the user is directed to the location where the first target image is output, based on the gaze information;
according to a first result of the determination, determine an impaired area of an entire visual field;
store a vision map based on the impaired area; and
control the optical engine to output a guidance image for notifying the user of the impaired area through the waveguide, based on the vision map, wherein the guidance image indicates an outline of the impaired area in a real scene seen by the user.

2. The electronic device of claim 1, further comprising a depth sensor, wherein the processor is further configured to execute the one or more instructions to:
control the optical engine to output a second target image through the waveguide;

output guidance information related to the second target image;
obtain, by using the depth sensor, a gesture input of the user associated with the guidance information;
obtain a user input pattern based on the gesture input of the user;
compare the second target image to the user input pattern; and
determine the impaired area based on a second result of the comparison.

3. The electronic device of claim 2, wherein the processor is further configured to execute the one or more instructions to:
determine an area where the second target image does not match the user input pattern;
determine the impaired area based on the area where the second target image does not match the user input pattern; and
determine a degree of distortion in the impaired area based on a distance between the second target image and the user input pattern.

4. The electronic device of claim 1, wherein the entire visual field comprises an entire display area on the waveguide, and
wherein the preset different locations comprise at least one of a plurality of locations spaced apart from each other at certain intervals on the waveguide.

5. The electronic device of claim 1, wherein the impaired area comprises at least one of a lost area or a distorted area.

6. An electronic device comprising:
a display comprising an optical engine and a waveguide;
a gaze tracking sensor;
a depth sensor;
a varifocal lens;
a memory configured to store one or more instructions; and
a processor configured to execute the one or more instructions to:
control the optical engine to output a first target image through the waveguide at preset different locations;
obtain gaze information of eyes of a user corresponding to a location of the first target image by using the gaze tracking sensor;
determine whether a gaze of the eyes of the user is directed to the location where the first target image is output, based on the gaze information;
according to a first result of the determination, determine an impaired area of an entire visual field;
store a vision map based on the impaired area;
detect an object comprised in the impaired area, based on the vision map by using the depth sensor;
apply a prism mode to at least a partial area of the varifocal lens corresponding to the impaired area in such a manner that an image of the object is refracted and moved to a normal area; and
control the optical engine to display a virtual image indicating that the image of the object is moved to the normal area of the entire visual field.

7. The electronic device of claim 6, wherein the prism mode is a mode in which refractive power of at least the partial area of the varifocal lens is changed, and
wherein the refractive power of the varifocal lens is changed by changing orientation of liquid crystal (LC) molecules in the varifocal lens.

8. A method of operating an electronic device, the method comprising:
controlling an optical engine to output a first target image through a waveguide at preset different locations;
obtaining gaze information of eyes of a user corresponding to a location of the first target image by using a gaze tracking sensor when the first target image is output;
determining, based on the gaze information, whether a gaze of the eyes of the user is directed to the first target image;
according to a first result of the determination, determining an impaired area of an entire visual field;
storing a vision map based on the impaired area; and
controlling the optical engine to output a guidance image for notifying the user of the impaired area through the waveguide, based on the vision map, wherein the guidance image indicates an outline of the impaired area in a real scene seen by the user.

9. The method of claim 8, comprising:
controlling the optical engine to output a second target image through the waveguide;
outputting guidance information related to the second target image;
obtaining, by using a depth sensor, a gesture input of the user associated with the guidance information;
obtaining a user input pattern based on the gesture input of the user;
comparing the second target image to the user input pattern; and
determining the impaired area based on a second result of the comparison.

10. The method of claim 9, wherein the determining of the impaired area comprises:
determining an area where the second target image does not match the user input pattern;
determining the impaired area based on the area where the second target image does not match the user input pattern; and
determining a degree of distortion in the impaired area based on a distance between the second target image and the user input pattern.

11. The method of claim 8, comprising:
detecting an object comprised in the impaired area, based on the vision map by using a depth sensor;
applying a prism mode to at least a partial area of a varifocal lens corresponding to the impaired area in such a manner that an image of the object is refracted and moved to a normal area; and
controlling the optical engine to display a virtual image indicating that the image of the object is moved to the normal area of the entire visual field.

12. The method of claim 11, wherein the prism mode is a mode in which refractive power of at least the partial area of the varifocal lens is changed, and
wherein the refractive power of the varifocal lens is changed by changing orientation of liquid crystal (LC) molecules in the varifocal lens.

13. A non-transitory computer-readable recording medium having recorded thereon a computer program for executing the method of claim 9.

* * * * *